US012662626B2

(12) United States Patent
Nierth

(10) Patent No.: US 12,662,626 B2
(45) Date of Patent: Jun. 23, 2026

(54) DICATIONIC FLUORESCENT DYES

(71) Applicant: Roche Molecular Systems, Inc., Pleasanton, CA (US)

(72) Inventor: Alexander Nierth, Dublin, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 889 days.

(21) Appl. No.: 17/756,810

(22) PCT Filed: Dec. 7, 2020

(86) PCT No.: PCT/EP2020/084930

§ 371 (c)(1),
(2) Date: Jun. 2, 2022

(87) PCT Pub. No.: WO2021/116037

PCT Pub. Date: Jun. 17, 2021

(65) Prior Publication Data

US 2023/0050863 A1 Feb. 16, 2023

Related U.S. Application Data

(60) Provisional application No. 62/945,456, filed on Dec. 9, 2019.

(51) Int. Cl.

| | |
|---|---|
| ***C09K 11/06*** | (2006.01) |
| ***C09B 11/28*** | (2006.01) |
| ***C12Q 1/68*** | (2018.01) |
| ***C12Q 1/6851*** | (2018.01) |
| ***G01N 33/533*** | (2006.01) |

(52) U.S. Cl.

CPC .............. *C09K 11/06* (2013.01); *C09B 11/28* (2013.01); *C12Q 1/6851* (2013.01); *G01N 33/533* (2013.01); *C09K 2211/1018* (2013.01); *C12Q 2600/16* (2013.01)

(58) Field of Classification Search

CPC ....... C09K 11/06; C09B 11/28; C12Q 1/6851; C12Q 1/686; G01N 33/533

See application file for complete search history.

(56) References Cited

U.S. PATENT DOCUMENTS

| | | | |
|---|---|---|---|
| 6,133,445 A | 10/2000 | Waggoner et al. | |
| 7,964,361 B2 | 6/2011 | Waggoner et al. | |
| 9,139,868 B2 | 9/2015 | Zhou et al. | |
| 9,579,402 B2 | 2/2017 | Mao et al. | |
| 2011/0136201 A1* | 6/2011 | Mao .................. | C07D 491/147 544/405 |
| 2015/0276752 A1 | 10/2015 | Bertozzi | |
| 2018/0073064 A1 | 3/2018 | Kozlov et al. | |
| 2019/0100653 A1 | 4/2019 | Kemnitzer et al. | |
| 2019/0367737 A1 | 12/2019 | Butkevich et al. | |
| 2020/0087516 A1 | 3/2020 | Urano | |

FOREIGN PATENT DOCUMENTS

| | | |
|---|---|---|
| CN | 102712614 A | 10/2012 |
| CN | 105073761 A | 11/2015 |
| JP | 2010517318 A | 5/2010 |
| JP | 2016521254 A | 7/2016 |
| WO | 2008094399 A1 | 8/2008 |
| WO | 2011068569 A1 | 6/2011 |
| WO | 2014144793 A1 | 9/2014 |
| WO | 2018151260 A1 | 8/2018 |

OTHER PUBLICATIONS

Yuichiro Koide, et al. "Design strategy for germanium-rhodamine based pH-activatable near-infrared fluorescence probes suitable for biological applications" Communications Chemistry | (2019) 2:94 (Year: 2019).*

Butkevich, A.N. et al., "Two-Color 810 nm STED Nanoscopy of Living Cells with Endogenous Snap-Tagged Fusion Proteins", ACS Chem. Biol. 2018, 13, 475-480.

Zhang, H. et al., "Pyridine-Si-xanthene: A novel near-infrared fluorescent platform for biological imaging", Chinese Chemical Letters, 2019, 30, 1063-1066.

International Search Report for PCT/EP2020/084930, mailed Mar. 19, 2021.

Wang, et al, Photoluminescence Quenching of Conjugated Macromolecules by Bipyridinium Derivatives in Aqueous, American Chemical Society_Lamgmuir, vol. 17, No. 4, 2001 1262-1266.

Song, et al_7-Azabicyclo[2.2.1]heptane as a Unique and Effective Dialkylamino Auxochrome Moiety: Demonstration in a Fluorescent Rhodamine Dye_J. Am. Chem. Soc. 2008, 130, 52, 17652-17653.

Rusha, et al_ Design and application of esterase-labile sulfonate protecting groups_Chem. Commun., 2011,47, 2038-2040.

Bunting, et al_Fluorescent cationic probes of mitochondria. Metrics and mechanism of interaction_Biophys J. 1989 vol. 56(5):979-993.

* cited by examiner

*Primary Examiner* — Jezia Riley
(74) *Attorney, Agent, or Firm* — Daniel E. Agnew

(57) ABSTRACT

The present invention provides for water-soluble mono- and dicationic fluorescent dyes with the latter exhibiting stable fluorescence at elevated temperatures. The present invention also provides for methods for the production of the fluorescent dyes and for using these dyes in biological assays such as multiplexing qPCR and tissue staining.

13 Claims, 6 Drawing Sheets

(1) (2) (3)

(3) (4)

(3) (5)

(3) (6)

DICATIONIC FLUORESCENT DYES

CROSS REFERENCE TO RELATED APPLICATIONS

This application is a U.S. national stage filing under 35 U.S.C. § 371 of International Application No. PCT/EP2020/084930, filed Dec. 7, 2020, entitled "DICATIONIC FLUORESCENT DYES", which claims the benefit of priority to U.S. Provisional Patent Application No. 62/945,456, filed on Dec. 9, 2019, each of which is hereby incorporated in its entirety by reference.

FIELD OF THE INVENTION

The present invention relates generally to fluorescent compounds. In particular, the present invention relates to rhodamine-based fluorescent dyes as well as methods for synthesizing and using these dyes.

BACKGROUND OF THE INVENTION

Fluorescent dyes with tailored properties are important to virtually any analytical method that relies on detection of fluorescence light. In the life sciences, the applications of fluorescent dyes range from real-time polymerase chain reaction (PCR) assays to fluorescence imaging techniques (including, but not limited to fluorescent microscopy, single-molecule imaging, super-resolution microscopy, and labeling and tracking experiments in cells).

Current advancements in the field of analytical PCR are directed towards multiplexing, i.e. the simultaneous detection of multiple targets in analytical samples. PCR with TAGS (Temperature Assisted Generation of Signal, disclosed in U.S Patent Publication No. 2018/0073064 and incorporated by reference herein in its entirety) is a multiplexing technology that enables the measurement of multiple individual targets in each fluorescence channel by collecting fluorescence data at different temperatures during thermal cycling. Consequently, TAGS multiplexing with two or three temperature channels can double or triple the number of resolvable targets per optical channel. In principle, this technology can be deployed on any quantitative PCR (qPCR) instrument capable of collecting more than one fluorescence read per PCR cycle.

As for any application that relies on fluorescence detection, PCR with TAGS technology requires bright dyes. The brightness of a fluorophore is defined by the product of its extinction coefficient and quantum yield. While the extinction coefficient determines the efficiency of the fluorophore to absorb excitation light, the quantum yield is a measure of how many photons the fluorophore emits per excitation event. It is a common problem that the overall brightness of fluorophores tends to decrease significantly when moving towards the red end of the electromagnetic spectrum. Consequently, fluorophores in the near-infrared (NIR) spectral range (excitation and emission between 650 and 900 nm) suffer from decreased brightness, thus lowering the overall sensitivity for fluorescence-based applications.

Another requirement for fluorescent dyes in the context of PCR with TAGS technology is temperature-stable fluorescence emission. Particularly cyanine dyes such as Cy5, Cy5.5, or Cy7 exhibit significant loss of brightness at elevated temperatures; a characteristic inherent to the polymethine scaffold with its conformationally flexible chain of conjugated double bonds.

Yet another requirement is the minimization of background fluorescence from the quenched probes, i.e. before cleavage and unquenching by the polymerase. The background fluorescence scales with the number of PCR probes and leads to an overall reduction of the measurable signal gain per target. As such, the accumulation of residual fluorescence depends on the efficiency by which each fluorophore is quenched, and this is not only a function of the molecular distance, but also dependent on the nature of the fluorophore-quencher pair.

The fluorescent dyes discussed in the present disclosure address these key issues by introducing two structural changes to the base structure of common rhodamines. The oxygen was substituted by silicon or germanium, whereas the aryl group was exchanged by imidazole or imidazolium heterocycles. The combined action of both modifications led to unusually red-shifted rhodamines that are smaller in size than typical fluorophores for this wavelength range.

The water-solubility of fluorescent dyes is a prerequisite for any application where water is the primary solvent and is often accomplished by decorating the chromophore with negatively charged functional groups such as carboxylates or sulfates. With the introduction of a second positive charge by the imidazolium moiety and the compact size, chromophores with exceptionally high water-solubility are obtained. Dye size, charge, and solubility are also important parameters in the context of fluorescence microscopy, with significant influence on tissue, cell or organelle penetration. For example hydrophobicity can also cause misleading fluorescence signals due to aggregation or strong interactions of the target with lipid bilayers.

The mono- and dicationic dyes in the present disclosure expand on the number of available fluorophore scaffolds in the far-red to NIR spectral range. The thermostability of fluorescence, improved background fluorescence and high water-solubility make these dyes useful for multiplexing PCR and fluorescence microscopy.

SUMMARY OF THE INVENTION

The present invention relates to novel rhodamine-based fluorescent dyes as well as methods for synthesizing and using these dyes.

In one aspect, the present invention provides for fluorescent dyes of Formula A:

Formula A

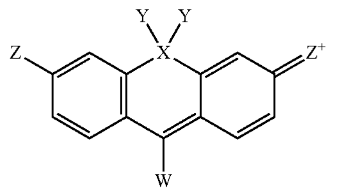

wherein:

X=Si, Ge, or C;

Y=Me, Et, iPr, or phenyl;

Z=any one of:

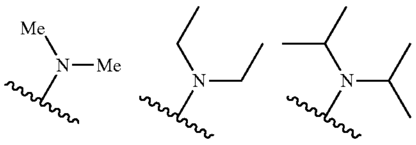

-continued
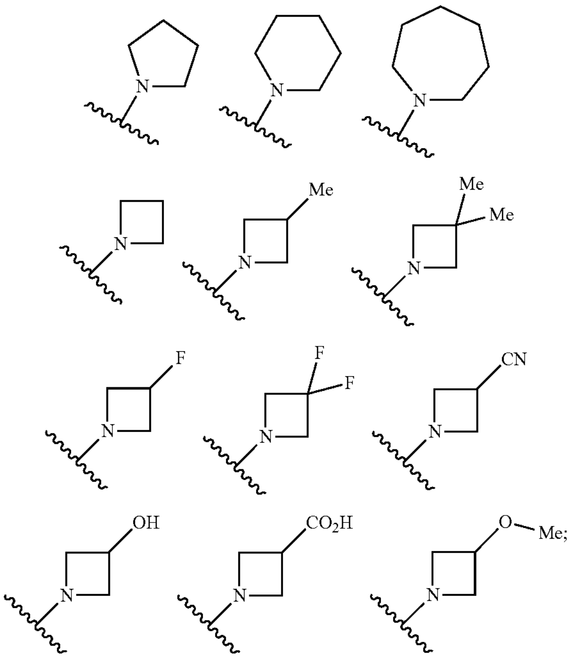
W=any one of:
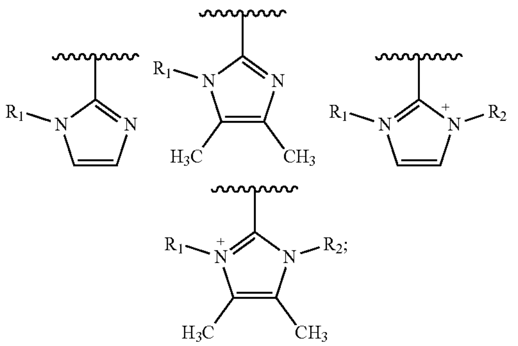
$R_1$ and $R_2$ are any combination of:
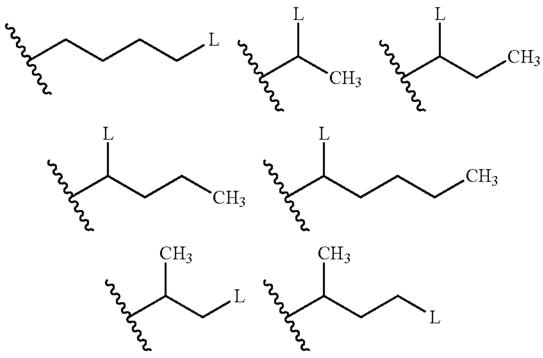
-continued
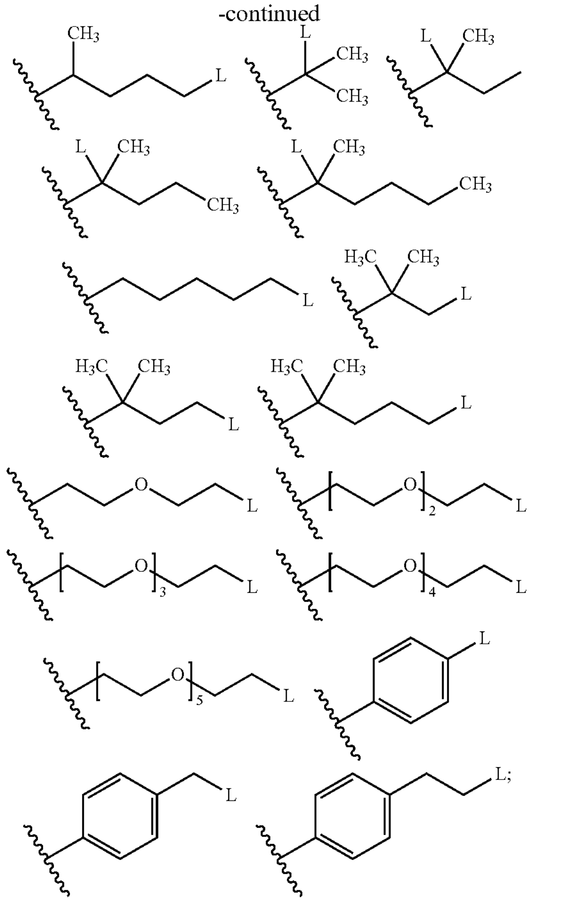
L=H, $SO_3H$, $CONH_2$, $CO_2H$, $N_3$, or any moiety subject to click chemistry functionality.
In another aspect, the present invention provides for fluorescent dyes of Formula B
Formula B
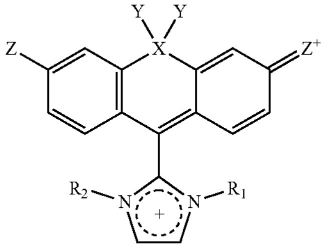
wherein:
X=Si, Ge, or C;
Y=Me, Et, iPr, or Ph;
Z=any one of:
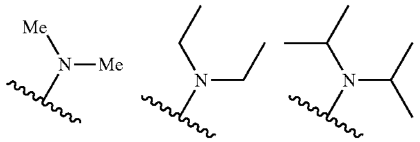

-continued
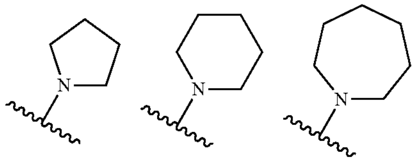
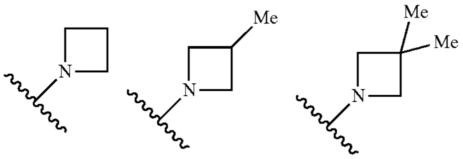
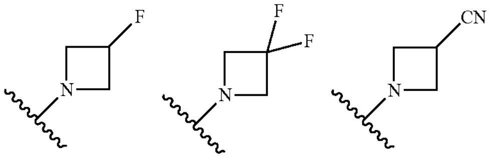
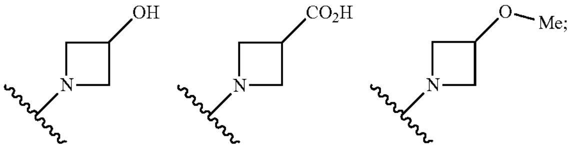
$R_1$ and $R_2$ are any combination of:
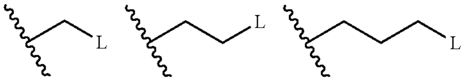
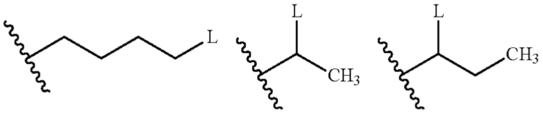
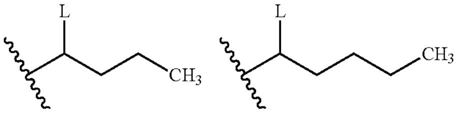
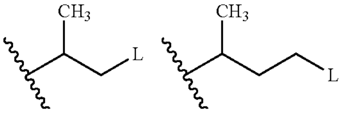
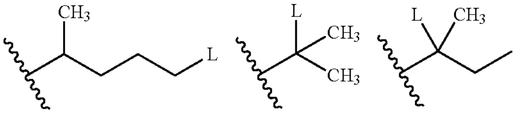
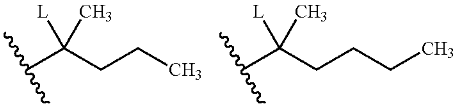
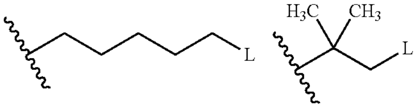
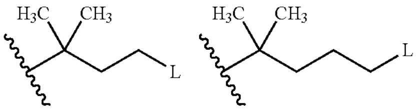
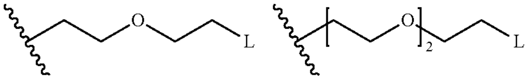
-continued
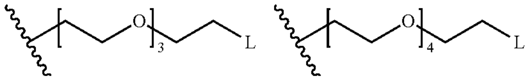
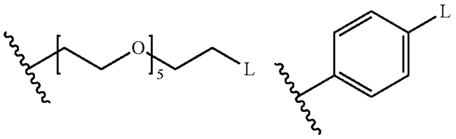
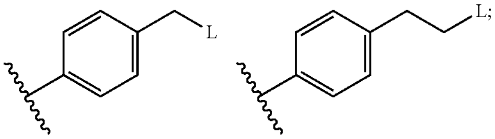
L=H, $SO_3H$, $CONH_2$, $CO_2H$, $N_3$, or any moiety subject to click chemistry functionality.
In one embodiment, Z=any one of:
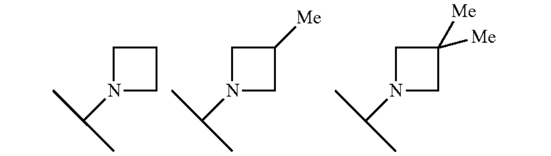
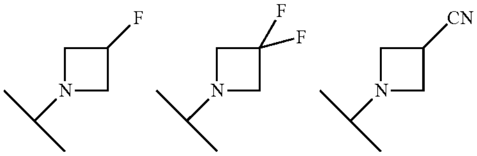
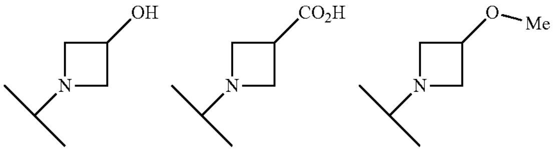
In another embodiment, Z=
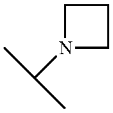
In another aspect, the present invention provides for fluorescent dyes selected from the following structures:
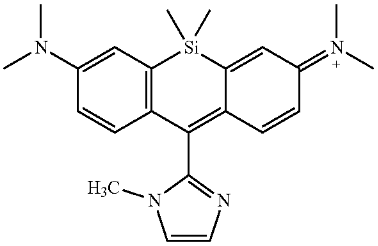

-continued

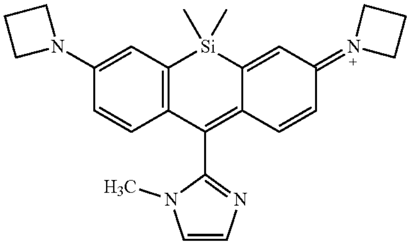

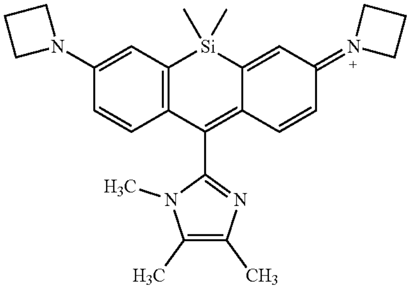

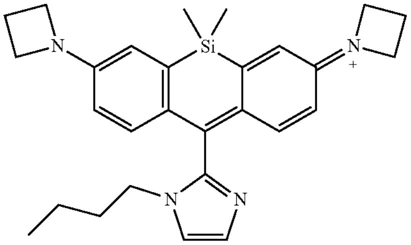

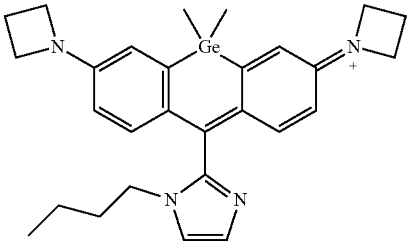

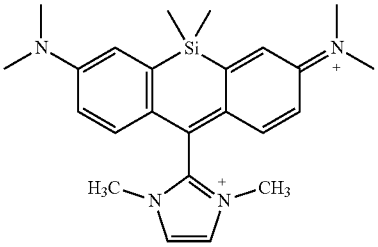

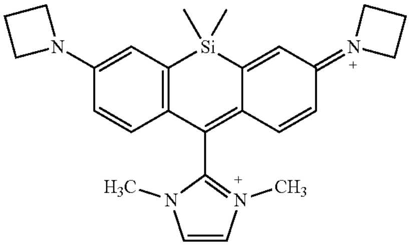

-continued

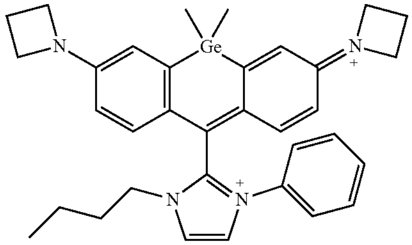

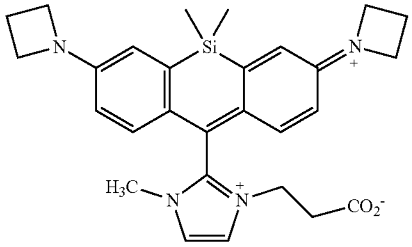

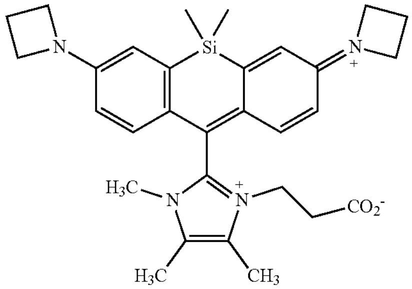

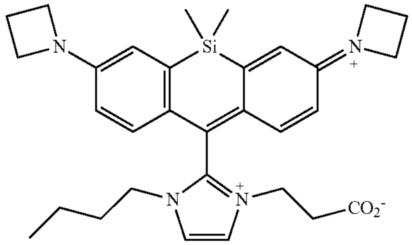

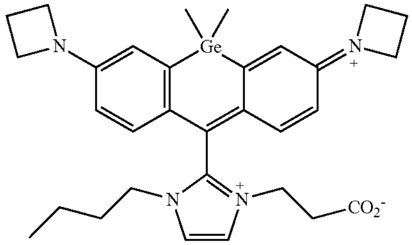

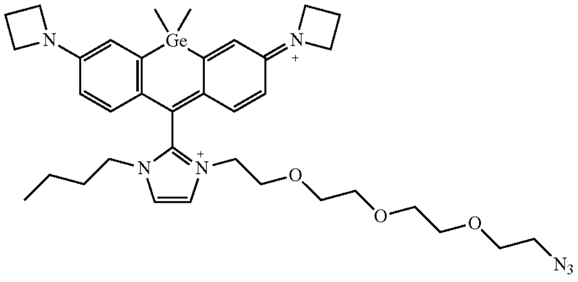

In another aspect, the present invention provides methods for preparing the fluorescent dyes of the present invention. Herein, the method for preparing the fluorescent dyes may comprise the steps described in Examples 4, 5, 6, 7 or 8. In yet another aspect, the present invention provides for the use of the fluorescent dyes of the present invention. In one embodiment, the use of the fluorescent dyes of the present invention is for the detection of one or more target nucleic acids in a sample by PCR assays, particularly in multiplex PCR assays. In another embodiment, the detection of target nucleic acids in PCR assays by the fluorescent dyes of the present invention can be performed at elevated (e.g. 65° C. and above) temperatures. In one embodiment, the use of the fluorescent dyes of the present invention is for the detection of one or more target proteins in a tissue sample by immunohistochemical assay. In another embodiment, the detection of target proteins in the immunohistochemical assay employs primary or secondary antibodies labeled by the fluorescent dyes of the present invention.

DETAILED DESCRIPTION OF THE INVENTION

Definitions

Figure 1:
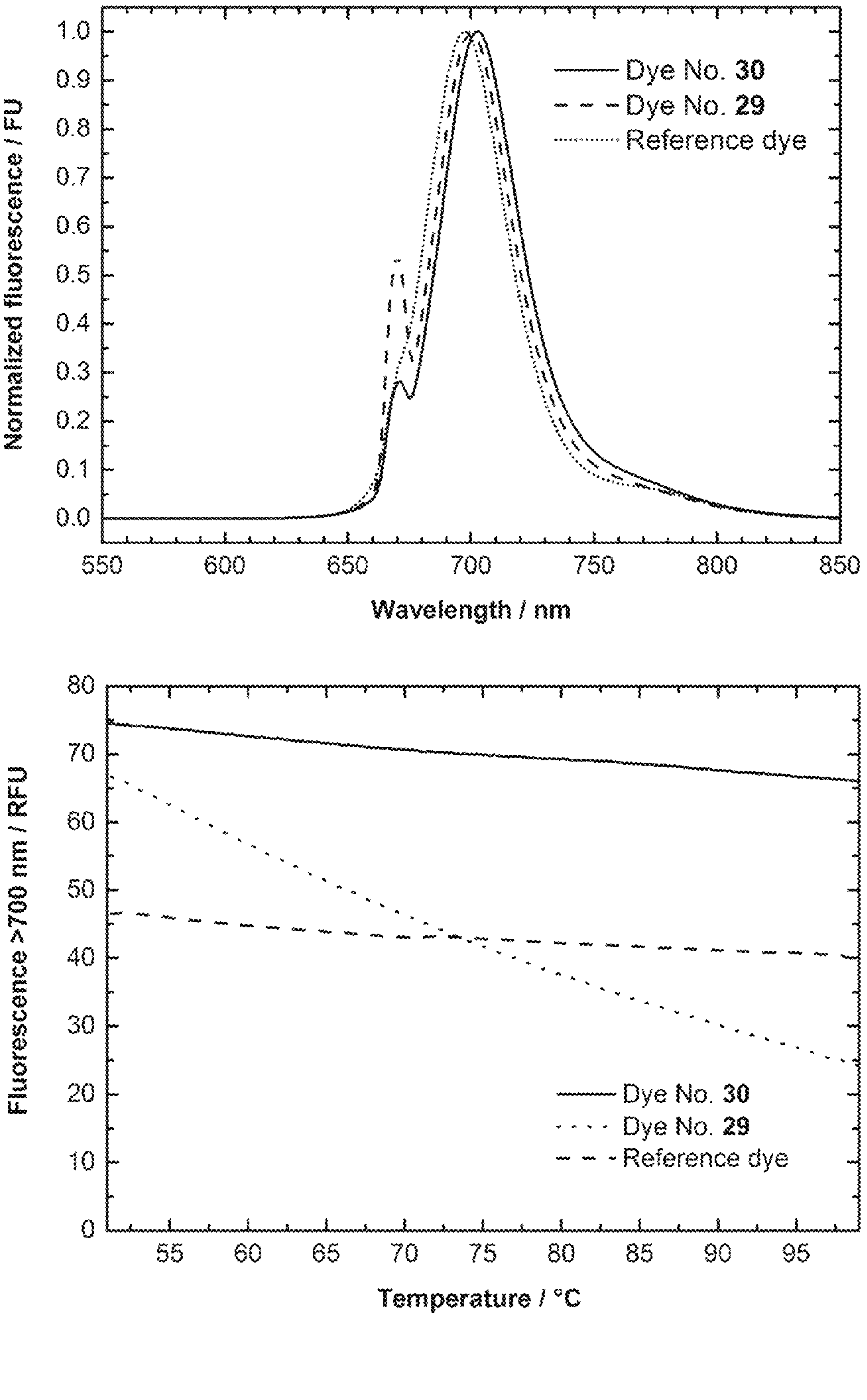
FIG. 1: The top panel shows fluorescence spectra for two representative fluorescent dyes Nos. 29, 30, and a commercially available reference dye. The bottom panel shows the temperature dependency of fluorescence for the same set of dyes. These results show that the fluorescent dyes with azetidine modification show improved thermostability of fluorescence.

Unless defined otherwise, all technical and scientific terms used herein have the same meaning as commonly understood by one of ordinary skill in the art to which this invention pertains. Although essentially any methods and materials similar to those described herein can be used in the practice or testing of the present invention, only exemplary methods and materials are described. For purposes of the present invention, the following terms are defined below.

The terms "a," "an," and "the" include plural referents, unless the context clearly indicates otherwise.

As used herein and unless otherwise indicated, the term "alkyl group" means a saturated, monovalent, unbranched or branched hydrocarbon chain. Examples of alkyl groups include, but are not limited to, C1-C6 alkyl groups, such as methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2 pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl, and longer alkyl groups, such as heptyl, and octyl. An alkyl group can be unsubstituted or substituted with one or two suitable substituents.

As used herein and unless otherwise indicated, the chemical symbols "Si" and "Ge" refer to silicon and germanium, respectively. Also, as used herein, "Me" refers to methyl, "Et" refers to ethyl, "iPr" refers to isopropyl, "Ph" refers to phenyl.

As used herein and unless otherwise indicated, the term —O-alkyl (or alkyl-O—) means an "alkoxy group," wherein alkyl is as defined above. An alkoxy group can be unsubstituted or substituted with one or more suitable substituents. The alkyl chain of an alkoxy group can be, for example, from 1 to 6 carbon atoms in length.

As used herein and unless otherwise indicated, the term "metal" refers to a group I or group II metal, including but not limited to, $Li^+$, $Na^+$, $Ca^{2+}$, or $Mg^{2+}$.

As used herein and unless otherwise indicated, the term "linking group" and "linker" are used interchangeably and refer to a moiety of a detectable label capable of covalently bonding a base with a label, e.g., forming a "linkage" that connects the nucleoside, nucleotide or nucleic acid to the label. Examples of linkers include, but are not limited to, O, S, or NH. Optionally, the linking group or linker is a covalent bond (i.e., the label is covalently bonded to the base).

As used herein and unless otherwise indicated, the term "counterion" refers to an ion that is stable and synthetically accessible. Examples of counterions include, but are not limited to chloride, bromide, iodide, sulfate, benzene sulfonate, p-toluenesulfonate, p-bromobenzenesulfonate, methanesulfonate, trifluoromethanesulfonate, phosphate, perchlorate, tetrafluoroborate, hexafluorophosphate, tetraphenylboride, nitrate and anions of aromatic or aliphatic carboxylic acids.

The terms "click chemistry", "click reaction" and "click chemistry reaction" are used interchangeably and refers to the [3+2] cycloaddition between alkynes and azides, a reaction which has allowed remarkable selectivity in conjugation reactions in biological samples as first described by Rostovtsev et al., Angew. Chem. Int. Ed., 2002, 41, 2596-2599, hereby incorporated by reference, in its entirety. Although early click chemistry reactions utilized copper as catalyst, copper-free click chemistry reactions are preferred in nucleic acid studies and the use of dibenzocyclooctyne (DBCO) derivatives are described in WO2009/067663 (incorporated by reference, in its entirety). Reagents such as DBCO-deoxythymidine (DBCO-dT) and DBCO-serinol are available as phosphoramidites for oligonucleotide synthesis from Glen Research (Sterling, VA).

The compounds according to the invention provide molecules that are, due to their spectral properties (absorption maxima within the region of approx. 650 nm and above as well as emission maxima above 670 nm), very suitable as dyes and particularly as fluorescence dyes. Particularly preferred are absorption maxima at approximately 700 nm. At the same time, the spectral properties of the molecules can be changed by the fact that the identity, number and position of the residues with respect to Z, W, $R_1$, and $R_2$ is changed. This way, fluorescence dyes can be produced with almost any absorption and emission maximum above 650 nm. A subject matter of the invention therefore also is the use of the rhodamine derivatives according to the invention as a fluorescence dye or as a laser dye.

Among the compounds according to the invention of the general Formula A or B at least one of the residues $R_1$ or $R_2$ is preferably present in the form of an activated group suitable for coupling or in the form of a group which can be activated for coupling. Such an activated group is particularly derived from a carboxylic-acid or sulfonic acid group which can be activated, and can for example be an acid ester, an acid anhydride, an acid halogenide, preferably bromide, in particular chloride or an N-hydroxysuccinimide ester or an ω-alkylhalogenide. Furthermore, such an activated group can for example also be phosphoramidites.

For the production of conjugates containing the rhodamine derivatives according to the invention activated derivatives, which are for example, suitable for biomolecule labeling or labeling of other analytic reagents can be synthesized. The production of the activated derivatives requires at least one of the groups capable of being activated, where activation is performed according to standard protocols known to the expert. Depending on the subsequent application, different reactive groups can be introduced. Phosphoramidites and H-phosphonates can for example be derived from a hydroxyl group. The production of rhodamine phosphoramidites and, respectively H-phosphonates is thus generally performed according to hitherto known protocols (Methods in Mol. Biol. Vol 20. "Protocols for Oligonucleotides and Analogs, Synthesis and Properties". S. Agrawal Hrsg., Humana Press Totowa, N.J.).

N-hydroxysuccinimide (NHS) esters are however generally derived from a carboxyl group, maleimides from an amino group (P. Y. Reddy, Synthesis (1998) 999) or by extension of an activated carboxylic acid with the corresponding ω-aminoalkylmaleimide.

The production of NHS-esters is preferably performed according to the method described in EP0543333, where the free carboxylic acid is admixed with NHS in the presence of a condensation reagent such as for example DCC or MEL. The production of rhodamine isothiocyanates is preferably carried out by the reaction of amino groups with thiophosgene (Advanced Organic Chemistry, Mc Graw Hill, 2. sup. nd edition. p. 383, 1997).

The subject matter of the invention are therefore also activated derivatives of the rhodamines according to the invention. The reactive groups of the activated derivatives are preferably phosphoramidite, N-hydroxysuccinimide (NHS)-ester, maleimide-alkylamide, H-phosphonate or isothiocyanate or ω-alkylhalogenides.

A further subject matter of the invention are conjugates obtainable by the binding of rhodamine compounds according to the invention or activated derivatives thereof. Such conjugates are thus composed of at least two components, with one component representing a rhodamine derivative according to the invention. Starting from the activated derivatives the production of the conjugates is carried out according to standard protocols. The appropriate conjugation methods to be applied are known to the expert.

The conjugates according to the invention can be used for analytic purposes as soon as a second component of the conjugate can bind to a binding partner to be analyzed and the built complex can be identified by the detection of the fluorescence emitted by the built complex after excitation with light of an appropriate absorption wavelength.

Due to the absorption in the near-IR the compounds according to the invention are also suitable for the in vivo use. For this, water-soluble derivatives of the dyes according to the invention and conjugates thereof are applied together with biomolecules. The in-vivo measurements are carried out by measuring the fluorescence or the absorption.

The use of the conjugates according to the invention is particularly suitable for diagnostic analyses or for analyses of medical or biological material. A subject matter of the invention are therefore particularly those conjugates capable of interacting with a biomolecule. These are conjugates that in general also contain one or several biomolecules as a further component.

These biomolecules contained in the conjugates can for example be single- or double-stranded nucleic acids such as DNA, RNA or triplex structures or nucleic acid analogs such as PNA, oligonucleotides as well as oligonucleotide derivatives but also single nucleotides, nucleotide derivatives, nucleotide analogs or nucleoside triphosphates. Labeling of such molecules takes place at the 5'-position, preferably by an NHS ester or a phosphoramidite, at the 3'-position however preferably via a dye-substituted carrier material like for example CPG. Labeling of other places such as, e.g. nucleic bases is preferably carried out by an NHS ester, too.

In the case of labeling of proteins, protein complexes, antibodies or amino acids conjugation is preferably performed by an NHS ester, m-maleimides or an isothiocyanate or ω-alkylhalogenides. Examples of further conjugate components are vitamins, steroid hormones, lipid molecules as well as haptens. Moreover, more complex biological structures such as membrane fractions or whole cells can also be labeled.

A particular embodiment of the conjugates according to the invention are oligonucleotides conjugated with a rhodamine derivative according to the invention. Oligonucleotides marked this way can be used for hitherto known methods of detection and analysis of nucleic acids, for example by in situ hybridization (Meyne and Myzis, Methods Mol. Biol. 33. 63-74, 1994) or also as primers in different sequencing methods (Sheealy et al., Anal. Chem. 67, 247-251, 1995).

Besides chemical labeling of nucleic acids ribonucleoside triphosphates and, respectively, deoxyribonucleoside triphosphates marked with rhodamine dyes according to the invention can be inserted as substrates for polymerases in nucleic acids by different enzymatic reactions. For DNA this is achieved with DNA polymerases for example by applying the Nick Translation method (Rigby et al., J. Mol. Biol. 113, p. 237, 1977) or by "Random Primed Labeling" (Feinberg and Vogelstein. Anal. Biochem. 137. p. 266, 1984). In the case of RNA this is for example achieved with T3, T7 or SP6 RNA-polymerases by means of transcription. A further method of nucleic acid marking is possible by the so-called 3'-tailing-reaction using the terminal transferase.

A further subject matter of the invention thus also is the use of conjugates according to the invention for marking of nucleic acids by chemical or enzymatic methods as well as the use of hybridization probes labeled according to the invention for the detection and analysis of nucleic acids.

For an analytic assay the rhodamine derivative according to the invention is first excited with light of an appropriate wavelength like for example a laser, laser diodes or LEDs. Depending on the analyte the fluorescence detection is performed by means of measuring methods known to the expert. These are for example fluorescence microscopy for in-situ methods or the detection of the emitted radiation by appropriate photo diodes.

A further subject matter of the invention thus also is the use of dye conjugates for immunohistochemical staining of paraffin tissue sections. Immunohistochemistry allows the visualization of antigens via the sequential application of a specific antibody (primary antibody) that binds to the antigen, a secondary antibody (link antibody) that binds to the primary antibody, an enzyme complex and a chromogenic substrate with interposed washing steps. The enzymatic activation of the chromogen results in a visible reaction product at the antigen site.

Besides the direct excitation of the dye according to the invention using radiation energy of a suitable wavelength, excitation can also be achieved by the so-called fluorescence resonance energy transfer (also known as Forster resonance energy transfer). With this principle, a second fluorescence dye is excited with light of an appropriate wave length. Due to the local proximity of the two dyes a nonradiative energy transfer to the rhodamine derivative according to the invention takes place subsequently (Van der Meer et al., Resonance Energy Transfer, V C H, 1994). The detection of the light emitted by this molecule at a certain wavelength can be used preferably for the quantitative determination of the analyte. A subject matter of the invention therefore also is the use of a rhodamine derivative according to the invention or of the corresponding conjugate as a component of a fluorescence resonance energy transfer system.

The compounds according to the invention are applied as resonance energy donors or acceptors. Preferred resonance energy donors for all compounds according to the invention are fluorescence dye conjugates suitable for spectral analysis. A subject matter of the invention therefore also is the use of rhodamine derivatives according to the intention or of the corresponding conjugates together with appropriate fluorescence resonance donor conjugates as a fluorescence resonance energy acceptor in a fluorescence resonance energy transfer system.

For the quantitative detection of nucleic acids hybridization probes marked with fluorescence dyes such as oligonucleotides are suitable, which can be detected by the principle of the fluorescence resonance electron transfer (FRET). In the case of oligonucleotides, the terminal position 5' can for example be marked with one dye component of the FRET system and the 3' terminal position with the remaining dye component of the FRET system. The oligonucleotides can in this case also be marked within the sequence.

In a special embodiment such an oligonucleotide marked with two dyes is used during the nucleic acid amplification for the detection of the resulting products where the emission of the fluorescence resonance energy donor is determined. If the oligonucleotide is not bound to the target no donor fluorescence is measurable due to the nonradiative energy transfer. If however the oligonucleotide binds to the target DNA the two dye components are locally separated due to exonuclease activities of the DNA polymerase used so that a certain fluorescence degree of the FRET donor becomes measurable (U.S. Pat. No. 5,210,015).

In other preferred embodiments the different dyes are located at two different hybridization probes which can hybridize within local proximity to the target nucleic acid. These probes can for example be two oligonucleotide probes hybridizing to the same strand of the target nucleic acid, with the one dye at the 3' terminal nucleotide of the first probe and the other dye at the 5' terminal nucleotide of the second probe so that the distance between the two only consists of a small number of nucleotides, i.e. a number between 0 and 30. When using fluorescein combined with a rhodamine derivative according to the invention distances of 0-15, particularly of 1-5 nucleotides and in many cases of only one nucleotide have proven to be advantageous. If the nucleotide distances between the dye components are kept probes not being conjugated with the dye at the terminal end but internally can also be used.

In the case of double-stranded target-nucleic acids probes that bind to different strands of the target can also be used as far as there is a certain nucleotide distance of 0 to 30 nucleotides between the two dye components.

A further subject matter of the invention thus is the use of a conjugate according to the invention consisting of an oligonucleotide and a rhodamine derivative according to the invention for the analysis of nucleic acids where a further conjugate consisting of a second oligonucleotide and a further appropriate fluorescence dye is used and where after excitation of a dye preferably coupled to the second oligonucleotide a fluorescence resonance energy transfer can take place. Oligonucleotide combinations are in the following called "FRET pairs" and labeled as such.

It has been proven to be particularly advantageous to use such FRET pairs for the detection of amplification products during or after a polymerase chain reaction. A further subject matter of the invention is therefore the use of a conjugate according to the invention as a component of a FRET pair for the detection of reaction products of a nucleic acid amplification reaction. In a special test procedure one of the two amplification primers can at the same time be marked with one of the two dyes used and thus provide one of the two components of the FRET.

The use of suitable FRET pairs for the detection of the amplification products allows a so-called "Real-Time Monitoring" of PCR-reactions with determination of the data necessary for the amplification product generation depending on the number of reaction cycles primed. This is generally achieved by the fact that due to the reaction and temperature conditions during the annealing period needed for the amplification primers the oligonucleotides of the FRET pair also hybridize to the target nucleic acid and that with an appropriate excitation a measurable fluorescence signal is emitted. With the data obtained the amount of the target nucleic acid originally applied can be determined by quantitative analysis. Therefore, these embodiments are particularly important for quantitative RT-PCR experiments in which RNA concentrations of a biological sample are quantified. A subject matter of the invention therefore also is the use of conjugates according to the invention as a component of a FRET pair for the detection of reaction products of a nucleic acid amplification reaction where the reaction product is detected in each cycle. Additionally, a subject matter of the invention is the use of conjugates according to the invention as a component of a FRET pair for the performance of a quantitative determination of the nucleic acid to be amplified.

In a different embodiment the detection of the amplification product takes place after completion of the amplification reaction with continuous temperature increasing in the course of a fusion curve analysis after hybridization of the FRET pair to the target nucleic acid to be detected. Simultaneously, the fluorescence emitted depending on the temperature is determined. This enables the detection of sequences that—due to certain mismatches—hybridize less stringently with the FRET pair used. The fusion points determined this way can be used for the detection of point mutations or other polymorphisms. A subject matter of the intention therefore also is the use of conjugates according to the invention as a component of a FRET pair for the determination of fusion curves, in particular during the identification of polymorphisms and point mutations.

Such fluorescence resonance energy transfer processes can in general be used for the determination of molecule-molecule interactions such as e.g. protein-protein interactions or antigen-antibody reactions. A particular advantage is achieved when the reaction takes place under homogeneous conditions.

As a counterion each cation suitable for charge neutralization and compatible with the present anionic basic structure depending on the pH can be used.

The starting compounds are preferably selected in a way that the synthesis product contains a group suitable for activation. Such groups are activated according to known methods to obtain groups suitable for subsequent coupling with reactive groups of biologically active molecules to build biomolecule-dye conjugates. Between the activated groups and the biologically active molecules linkers can be inserted.

Linkers are used for variation of the distance between the dyes according to the invention and the biomolecules. Aminocaproic acid can for example be inserted in carboxylic acid for reasons of extension. This can also involve a change in functionality like for example by the reaction of the carboxylic acid with a maleinimidoalkylamine. Moreover, linker charges can effect the solubility of the dye. Amino acids with charge carriers such as lysin or glutamic acid are particularly suitable for this effect.

With the compounds according to the invention new compounds are provided that are—due to their spectroscopic properties (absorption maximum above 650 nm)—very appropriate as absorption dyes suitable for coupling, particularly as fluorescence dyes for the use in hapten-, antibody-, protein conjugates, and very suitable for polynucleotide marking and lattice dyeing (fluorescence latices).

Dyes of the rhodamine derivatives according to the invention are especially suitable for insertion in latices if they are soluble in organic, water-immiscible solvents and insertable in latices by a swelling procedure. Such fluorescent latices of a diameter of approx. 50 nm up to several μm can be loaded by means of different coating methods, e.g. with proteins, haptens or nucleic acids.

Dye mixtures with at least one dye according to the invention, so that a resonance energy transfer can take place.

Conjugates of the fluorescence dyes with haptens such as e.g. theophylline, digoxin, T3, T4 or proteins such as antibodies are for example suitable for use in diagnostic systems, in particular for fluorescence immunoassays fluorescence polarization immunoassays.

A further subject matter of the present invention is a procedure for the determination of a first, immunologically connectable substance wherein a conjugate of a compound according to the invention is used together with a second (immunologically) connectable substance which can be similar or different with regard to the first substance, and the absorption-, fluorescence- or fluorescence-polarization change of the compound according to the invention caused by an (immunological) binding reaction specific for the first substance is determined as a measure of the amount of the substance to be analyzed and contained in the sample.

A further subject matter of the invention is the use of the conjugates according to the invention in immunoassays.

As used herein, a substance that is "biologically compatible" is not toxic as used, and does not have a substantially deleterious effect on biomolecules.

As used herein and unless otherwise indicated, the term "nucleobase" refers to adenine, cytidine, guanine, thymine, or uracil.

As used herein and unless otherwise indicated, the term "nucleobase analog" refers to a substituted or unsubstituted nitrogen-containing parent heteroaromatic ring that is capable of forming Watson-Crick hydrogen bonds with a complementary nucleobase or nucleobase analog. Preferably, the nucleobase analog is a purine, deazapurine or pyrimidine. Exemplary nucleobase analogs include, but are not limited to, 7-deazaadenine, inosine, nebularine, nitropyrrole, nitroindole, 2-aminopurine, 2,6-diaminopurine, hypoxanthine, pseudouridine, 5-propynylcytidine, isocytidine, isoguanine, 7-deazaguanine, 2-thiopyrimidine, 6-thioguanine, 4-thiothymine, 4-thiouracil, $O^6$-methyl guanine, $N^6$-methyl adenine, $O^4$-methyl thymine, 5,6-dihydrothymine, 5,6-dihydrouracil, 4-methylindole, ethenoadenine, etc. Additional exemplary nucleobase analogs can be found in Fasman, 1989, Practical Handbook of Biochemistry and Molecular Biology, pp. 385-394, CRC Press, Boca Raton, FL, and the references cited therein, incorporated herein by reference.

As used herein and unless otherwise indicated, the term "nucleoside" refers to a compound consisting of a nucleobase covalently linked to the $C_1'$ carbon of a substituted or unsubstituted ribose sugar. Typical substituted ribose sugars include, but are not limited to, those in which one or more of its carbon atoms, preferably one and most preferably the 3' carbon atom, is substituted with one or more of the same or different —R, —OR, —NRR or halogen groups, where each R is independently —H, ($C_1$-$C_6$) alkyl or ($C_5$-$C_{14}$) aryl. Particularly preferred ribose sugars are ribose, 2'-deoxyribose, 2',3'-dideoxyribose, 3'-haloribose, 3'-fluororibose, 3'-chlororibose, 3'-alkylribose, etc. When the nucleobase is A or G, the ribose sugar is attached to the $N^9$ position of the nucleobase. Where the nucleobase is C, T or U, the pentose sugar is attached to the $N^1$ position of the nucleobase (see, e.g., Kornberg and Baker, 1992, DNA Replication, 2nd Ed., Freeman, San Francisco).

As used herein and unless otherwise indicated, the term "nucleoside analog" refers to a nucleoside in which the nucleobase, the ribose sugar, or both, are replaced with their respective analogs. Exemplary nucleobase analogs are those previously defined. Exemplary ribose sugar analogs include, but are not limited to, substituted or unsubstituted furanoses having more or fewer than five ring atoms, e.g., erythroses and hexoses and substituted or unsubstituted 3-6 carbon acyclic sugars. Typical substituted furanoses and acyclic sugars are those in which one or more of the carbon atoms are substituted with one or more of the same or different —R, —OR, NRR or halogen groups, where each R is independently H, ($C_1$-$C_6$) alkyl or ($C_5$-$C_{14}$) aryl.

As used herein and unless otherwise indicated, the term "nucleotide" refers to a nucleoside in which one or more, typically one, of the ribose carbons is substituted with a phosphate ester having the formula.

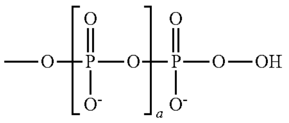

where a is an integer from 0 to 4. Preferably, a is 2 and the phosphate ester is attached to the 3' or 5' carbon of the ribose, e.g., ribose 3'-triphosphate, 2'-deoxyribose 3-triphosphate, ribose 5'-triphosphate, 2'-deoxyribose 5'-triphosphate, 3'-haloribose 5'-triphosphate, 3'-alkylribose 5'-triphosphate, 2',3'-dideoxyribose 5'-triphosphate, etc.

As used herein and unless otherwise indicated, the term "nucleotide derivative" refers to a nucleotide in which the nucleobase, the ribose sugar and/or one or more of the phosphate esters is replaced with its respective analog. Exemplary nucleobase and ribose sugar analogs are those previously described in conjunction with nucleoside analogs. Exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, peptide nucleic acid (PNA) monomers, etc., including any associated counterions, if present.

As used herein and unless otherwise indicated, the term "protecting group" means a group that is reversibly attached to a hydroxyl or amine moiety that renders the hydroxyl or amine moiety unreactive during a subsequent reaction(s) and that can be selectively cleaved to regenerate the hydroxyl or amine moiety once its protecting purpose has been served. Examples of protecting groups are found in Greene, T. W., Protective Groups in Organic Synthesis, 3rd edition (1999), incorporated herein by reference. In one embodiment, the protecting group is stable in a basic reaction medium, but can be cleaved by acid. Examples of base-stable, acid-labile protecting groups suitable for use with the invention include, but are not limited to, ethers, such as methyl, methoxy methyl, methylthiomethyl, methoxyethoxymethyl, bis(2 chloroethoxy)methyl, tetrahydropyranyl, tetrahydrothiopyranyl, tetrahydrofuranyl, tetrahydrothiofuranyl, 1-ethoxyethyl, 1-methyl 1-methoxyethyl, t-butyl, allyl, benzyl, o-nitrobenzyl, triphenylmethyl, α-naphthyldiphenylmethyl, p-methoxyphenyldiphenylmethyl, 9-(9-phenyl-10-oxo)anthranyl, trimethylsilyl, isopropyldimethylsilyl, t-butyldimethylsilyl, t-butyldiphenylsilyl, tribenzylsilyl, and triisopropylsilyl; and esters, such as pivaloate, adamantoate, and 2,4,6-trimethylbenzoate.

As used herein and unless otherwise indicated, the term "salt(s)," includes, but is not limited to, salts of acidic or basic groups that may be present in the compounds of the invention. Compounds that are basic in nature are capable of forming a wide variety of salts with various inorganic and organic acids. The acids that may be used to prepare acceptable acid addition salts of such basic compounds are those that form nontoxic acid addition salts, i.e., salts containing pharmacologically acceptable anions, including, but not limited to, sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartarate, oleate, tannate, pantothenate, bitartarate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds of the invention that include an amino moiety also can form acceptable salts with various amino acids, in addition to the acids mentioned above. Compounds of the invention that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

As used herein and unless otherwise indicated, the term "solvate" means a compound of the invention or a salt thereof, that further includes a stoichiometric or non stoichiometric amount of a solvent bound by non-covalent intermolecular forces. Preferred solvents are volatile and non-toxic. The term solvate includes hydrates. Hydrate means a compound of the invention or a salt thereof, that further includes a stoichiometric or non-stoichiometric amount of water bound by non-covalent intermolecular forces.

As used herein and unless otherwise indicated, the term "nucleoside or nucleotide" refers to nucleosides and/or nucleotides and/or mixtures thereof.

"Nucleoside analog" refers to a nucleoside in which the nucleobase, the ribose sugar, or both, are replaced with their respective analogs. Exemplary nucleobase analogs are those previously defined.

Exemplary ribose sugar analogs include, but are not limited to, substituted or unsubstituted furanoses having more or fewer than five ring atoms, e.g., erythroses and hexoses and substituted or unsubstituted 3-6 carbon acyclic sugars. Typical substituted furanoses and acyclic sugars are those in which one or more of the carbon atoms are substituted with one or more of the same or different —R, —OR, —NRR or halogen groups, where each R is independently H, $C_1$-$C_6$ alkyl or $C_5$-$C_{14}$ aryl.

As used herein and unless otherwise indicated, the term "nucleotide analog" refers to a nucleotide in which the nucleobase, the ribose sugar and/or one or more of the phosphate esters is replaced with its respective analog. Exemplary nucleobase and ribose sugar analogs are those previously described in conjunction with nucleoside analogs. Exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, peptide nucleic acid (PNA) monomers, etc., including any associated counterions, if present.

As used herein and unless otherwise indicated, the term "nucleic acid" refers to a linear polymeric chain of nucleoside monomer units that are covalently connected to one another by phosphate ester internucleotide linkages. Unless stated otherwise, "nucleic acid" as used herein includes polymers of any length, including oligonucleotides, nucleic acids and nucleic acids as those terms are commonly used in the art. Thus, nucleic acids according to the invention can range in size from a few monomer units (e.g., 4 to 40), to several hundreds of monomer units, to several thousands of monomer units, or even more monomer units. Such nucleic acids can also be described herein in terms of their functions, such as primer or probe. Whenever a nucleic acid is represented by a sequence of letters, e.g., "ATGCCTG," it will be understood that the sequence is presented in the 5'→3' direction. Unless otherwise indicated, nucleic acids whose sequences are described herein are 2'-deoxyribonucleic acids.

As used herein and unless otherwise indicated, the term "nucleic acid analog" refers to a nucleic acid in which at least one nucleoside monomer unit is a "nucleoside analog" and/or at least one phosphate ester internucleotide linkage is a phosphate ester analog, as defined above under "nucleotide analog." Preferred classes of nucleic acid analogs are those in which the sugar and internucleotide linkages are replaced with an uncharged, neutral amide, such as a morpholino carbamate and peptide nucleic acids ("PNA"). Preferred PNAs are those having a N-(2-aminoethyl) glycine amide backbone (see, e.g., Nielsen et al., 1991, Science 254:1497-1500).

As used herein and unless otherwise indicated, the term "label" refers to a detectable molecule or atom attached, covalently or non-covalently, to a nucleoside or nucleotide, nucleoside or nucleotide analog, nucleic acid, nucleic acid analog or terminator. In one embodiment, a nucleoside or nucleotide, nucleoside or nucleotide analog, nucleic acid, nucleic acid analog or terminator has a detectable label covalently attached to the nucleobase. The term "label" can also refer to a molecule that modulates detection of another detectable label, such as a quencher. As used herein, the term "detectable label" is intended to include not only a molecule or label which is "directly" detected (e.g., a chromogen or a fluorophore) but also a moiety (e.g., biotin) which is "indirectly" detected by its binding to a second, third, or greater binding partner (e.g., avidin or streptavidin), one of which carries a "direct" label.

Other examples of labels include a fluorescent compound, which, when exposed to light of the proper wavelength, becomes detectable due to fluorescence and is detected and/or measured by microscopy or fluorometry. Commonly used fluorescent labeling compounds include fluorescein isothiocyanate, rhodamine, phycoerythrin, phycocyanin, allophycocyanin, γ-phthalaldehyde and fluorescamine. The detectable label can be a fluorescence-emitting metal such as $^{152}Eu$, or others of the lanthanide series which can be attached to the oligonucleotide using metal chelating groups, such as diethylenetriaminepentaacetic acid or ethylenediaminetetraacetic acid.

The label can be a chemiluminescent compound, the presence of which is detected by measuring luminescence that arises during the course of a chemical reaction. Examples of useful chemiluminescent labeling compounds are luminol, isoluminol, theromatic acridinium ester, imidazole, acridinium salt and oxalate ester. Likewise, a bioluminescent compound can be used to label the oligonucleotide and is detected by measuring luminescence. In this case, a catalytic protein increases the efficiency of the chemiluminescence reaction. Examples of useful bioluminescent labeling compounds include luciferin, luciferase and aequorin.

As used herein and unless otherwise indicated, the term "reporter dye" refers to a compound which, when exposed to light, emits energy in the form of fluorescence. "The chromophore of a reporter dye" is the network of atoms of the reporter dye that, when exposed to light, emits radiation at a level that is detectable by conventional spectroscopic means.

As used herein and unless otherwise indicated, the term "non-fluorescent" refers to a compound that, when exposed to radiation, does not emit radiation at a level that is detectable by conventional spectroscopic means.

As used herein and unless otherwise indicated, the term "weakly fluorescent" refers to a compound that, when exposed to radiation, emits radiation at a low level that is detectable by conventional spectroscopic means.

As used herein and unless otherwise indicated, the term "light" refers to electromagnetic energy having a wavelength which causes a reporter dye to fluoresce, wherein that wavelength may be in the range of 190-800 nm.

As used herein and unless otherwise indicated, the term "specific" refers to a nucleic acid used in a reaction, such as a probe used in a hybridization reaction, a primer used in a PCR, or a nucleic acid present in a composition, that hybridizes only with the intended target but not to other nucleic acid molecules in the test sample in the normal testing environment.

As used herein and unless otherwise indicated, the term "selective" refers to a nucleic acid used in a reaction, such as a probe used in a hybridization reaction, a primer used in a PCR, or a nucleic acid present in a pharmaceutical preparation, that hybridizes with the intended target more frequently, more rapidly, or with greater duration than it does with other nucleic acids in the test sample in the normal testing environment.

As used herein, the term "hybridizes under stringent conditions" describes conditions for hybridization and washing under which nucleotide sequences at least 60% (65%, 70%, or 75% or greater) identical to each other typically remain hybridized to each other. Stringent conditions depend on the nature of the nucleic acid (e.g. length, GC content, etc.) and the method itself (hybridization, amplification, etc.).

Such methods are well known in the art and can be found in Current Protocols in Molecular Biology, John Wiley & Sons, N.Y. (1989), 6.3.1-6.3.6. In one embodiment, stringent hybridization conditions are hybridization at 6× sodium chloride/sodium citrate (SSC) at about 45° C., followed by one or more washes in 0.1×SSC, 0.2% SDS at about 68° C. In another embodiment, stringent hybridization conditions are hybridization in 6×SSC at about 45° C., followed by one or more washes in 0.2×SSC, 0.1% SDS at 50-65° C. (i.e., one or more washes at 50° C., 55° C., 60° C., or 65° C.). It is understood that the nucleic acids of the invention do not include nucleic acid molecules that hybridize under these conditions solely to a nucleotide sequence consisting of only A or T nucleotides. For example, stringent hybridization of an oligonucleotide of approximately 15-40 bases to a complementary sequence in the polymerase chain reaction (PCR) can be performed under the following conditions: a salt concentration of 50 mM KCl, a buffer concentration of 10 mM Tris HCl, a $Mg^{2+}$ concentration of 1.5 mM, a pH of 7-7.5 and an annealing temperature of 55-60° C. Moderate stringency hybridization of an oligonucleotide of approximately 15-40 bases to a complementary sequence in the polymerase chain reaction (PCR) can be performed under the following conditions: a salt concentration of 50 mM KCl, a buffer concentration of 10 mM Tris HCl, a $Mg^{2+}$ concentration of 1.5 mM, a pH of 7-7.5 and an annealing temperature of 48-54° C. Low stringency hybridization of an oligonucleotide of approximately 15-40 bases to a complementary sequence in the polymerase chain reaction (PCR) can be performed under the following conditions: a salt concentration of 50 mM KCl, a buffer concentration of 10 mM Tris HCl, a $Mg^{2+}$ concentration of 1.5 mM, a pH of 7-7.5 and an annealing temperature of 37-47° C.

As used herein and unless otherwise indicated, the term "stereomerically pure" refers to a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of stereoisomer of the compound and less than about 20% by weight of other stereoisomers the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

As used herein and unless otherwise indicated, the term "substantially free" refers to a composition that comprises one compound and is free of detectable or significant quantities of other compounds. A typical substantially free composition comprises greater than about 80% by weight of the desired compound and less than about 20% by weight of one or more other compounds, more preferably greater than about 90% by weight of the desired compound and less than about 10% by weight of one or more other compounds, even more preferably greater than about 95% by weight of the desired compound and less than about 5% by weight of one or more other compounds, and most preferably greater than about 97% by weight of the desired compound and less than about 3% by weight of one or more other compounds.

A method of nucleic acid amplification is the Polymerase Chain Reaction (PCR), which is disclosed, among other references, in U.S. Pat. Nos. 4,683,202, 4,683,195, 4,800,159, and 4,965,188. PCR typically employs two or more oligonucleotide primers that bind to a selected nucleic acid template (e.g. DNA or RNA). Primers useful for nucleic acid analysis include oligonucleotides capable of acting as a point of initiation of nucleic acid synthesis within the nucleic acid sequences of the target nucleic acids. A primer can be purified from a restriction digest by conventional methods, or it can be produced synthetically. The primer can be single-stranded for maximum efficiency in amplification, but the primer can be double-stranded. Double-stranded primers are first denatured, i.e., treated to separate the strands. One method of denaturing double stranded nucleic acids is by heating. A "thermostable polymerase" is a polymerase enzyme that is heat stable, i.e., it is an enzyme that catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have e.g. been isolated from *Thermus flavus, T. ruber, T. thermophilus, T. aquaticus, T. lacteus, T. rubens, Bacillus stearothermophilus*, and *Methanothermus fervidus*. Nonetheless, polymerases that are not thermostable also can be employed in PCR assays provided the enzyme is replenished.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 5 s to 9 min. In order to not expose the respective polymerase like e.g. the Z05 DNA polymerase to such high temperatures for too long and thus risking a loss of functional enzyme, it can be preferred to use short denaturation steps.

If the double-stranded template nucleic acid is denatured by heat, the reaction mixture is allowed to cool to a temperature that promotes annealing of each primer to its target sequence on the target nucleic acids.

The temperature for annealing can be from about 35° C. to about 70° C., or about 45° C. to about 65° C.; or about 50° C. to about 60° C., or about 55° C. to about 58° C. Annealing times can be from about 10 s to about 1 min. (e.g., about 20 s to about 50 s; about 30 s to about 40 s). In this context, it can be advantageous to use different annealing temperatures in order to increase the inclusivity of the respective assay. In brief, this means that at relatively low annealing temperatures, primers may also bind to targets having single mismatches, so variants of certain sequences can also be amplified. This can be desirable if e.g. a certain organism has known or unknown genetic variants which should also be detected. On the other hand, relatively high annealing temperatures bear the advantage of providing higher specificity, since towards higher temperatures the probability of primer binding to not exactly matching target sequences continuously decreases. In order to benefit from both phenomena, in some embodiments of the invention the process described above comprises annealing at different temperatures, for example first at a lower, then at a higher temperature. If, e.g., a first incubation takes place at 55° C. for about 5 cycles, non-exactly matching target sequences may be (pre-)amplified. This can be followed e.g. by about 45 cycles at 58° C., providing for higher specificity throughout the major part of the experiment. This way, potentially important genetic variants are not missed, while the specificity remains relatively high.

The reaction mixture is then adjusted to a temperature at which the activity of the polymerase is promoted or optimized, i.e., a temperature sufficient for extension to occur from the annealed primer to generate products complementary to the nucleic acid to be analyzed. The temperature should be sufficient to synthesize an extension product from each primer that is annealed to a nucleic acid template, but should not be so high as to denature an extension product from its complementary template (e.g., the temperature for extension generally ranges from about 40° to 80° C. (e.g., about 50° C. to about 70° C.; about 65° C.). Extension times can be from about 10 s to about 5 min., or about 15 s to 2 min., or about 20 s to about 1 min., or about 25 s to about 35 s. The newly synthesized strands form a double-stranded molecule that can be used in the succeeding steps of the reaction. The steps of strand separation, annealing, and elongation can be repeated as often as needed to produce the desired quantity of amplification products corresponding to the target nucleic acids. The limiting factors in the reaction are the amounts of primers, thermostable enzyme, and nucleoside triphosphates present in the reaction. The cycling steps (i.e., denaturation, annealing, and extension) can be repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

PCR can be carried out in which the steps of annealing and extension are performed in the same step (one-step PCR) or, as described above, in separate steps (two-step PCR). Performing annealing and extension together and thus under the same physical and chemical conditions, with a suitable enzyme such as, for example, the Z05 DNA polymerase, bears the advantage of saving the time for an additional step in each cycle, and also abolishing the need for an additional temperature adjustment between annealing and extension. Thus, the one-step PCR reduces the overall complexity of the respective assay.

In general, shorter times for the overall amplification can be preferred, as the time-to-result is reduced and leads to a possible earlier diagnosis.

Other nucleic acid amplification methods to be used comprise the Ligase Chain Reaction (LCR; Wu D. Y. and Wallace R. B., Genomics 4 (1989) 560-69; and Barany F., Proc. Natl. Acad. Sci. USA 88 (1991) 189-193); Polymerase Ligase Chain Reaction (Barany F., PCR Methods and Applic. 1 (1991) 5-16); Gap-LCR (WO 90/01069); Repair Chain Reaction (EP 0439182 A2), 3SR (Kwoh D. Y. et al., Proc. Natl. Acad. Sci. USA 86 (1989) 1173-1177; Guatelli J. C. et al., Proc. Natl. Acad. Sci. USA 87 (1990) 1874-1878; WO 92/08808), and NASBA (U.S. Pat. No. 5,130,238). Further, there are strand displacement amplification (SDA), transcription mediated amplification (TMA), and Qb-amplification (for a review see e.g. Whelen A. C. and Persing D. H., Annu. Rev. Microbiol. 50 (1996) 349-373; Abramson R. D. and Myers T. W., Curr. Opin. Biotechnol. 4 (1993) 41-47).

The terms "Cp value", "Ct value", "Cp", "Ct" or "crossing point" value refers to a value that allows quantification of input target nucleic acids. The Cp or Ct value can be determined according to the second-derivative maximum method (Van Luu-The et al., "Improved real-time RT-PCR method for high-throughput measurements using second derivative calculation and double correction," BioTechniques, Vol. 38, No. 2, February 2005, pp. 287-293). In the second derivative method, a Cp/Ct corresponds to the first peak of a second derivative curve. This peak corresponds to the beginning of a log-linear phase. The second derivative method calculates a second derivative value of the real-time fluorescence intensity curve, and only one value is obtained. The original Cp/Ct method is based on a locally defined, differentiable approximation of the intensity values, e.g., by a polynomial function. Then the third derivative is computed. The Cp/Ct value is the smallest root of the third derivative. The Cp/Ct can also be determined using the fit point method, in which the Cp/Ct is determined by the intersection of a parallel to the threshold line in the log-linear region (Van Luu-The et al., BioTechniques, Vol. 38, No. 2, February 2005, pp. 287-293). The Cp/Ct value provided by the LightCycler instrument offered by Roche by calculation according to the second-derivative maximum method.

The term "PCR efficiency" refers to an indication of cycle to cycle amplification efficiency. PCR efficiency is calculated for each condition using the equation: % PCR efficiency=$(10^{(-slope)}-1)\times100$, wherein the slope was calculated by linear regression with the log copy number plotted on the y-axis and Cp plotted on the x-axis. PCR efficiency can be measured using a perfectly matched or mismatched primer template.

The term "FRET" or "fluorescent resonance energy transfer" or "Forster resonance energy transfer" refers to a transfer of energy between at least two chromophores, a donor chromophore and an acceptor chromophore (referred to as a quencher). The donor typically transfers the energy to the acceptor when the donor is excited by light radiation with a suitable wavelength. The acceptor typically re-emits the transferred energy in the form of light radiation with a different wavelength. When the acceptor is a "dark" quencher, it dissipates the transferred energy in a form other than light. Whether a particular fluorophore acts as a donor or an acceptor depends on the properties of the other member of the FRET pair. Commonly used donor-acceptor pairs include the FAM-TAMRA pair. Commonly used quenchers are DABCYL and TAMRA. Commonly used dark quenchers include BlackHole Quenchers™ (BHQ), (Biosearch Technologies, Inc., Novato, Cal.), Iowa Black™ (Integrated DNA Tech., Inc., Coralville, Iowa), and BlackBerry™ Quencher 650 (BBQ-650) (Berry & Assoc., Dexter, Mich.).

The methods set out above can be based on Fluorescence Resonance Energy Transfer (FRET) between a donor fluorescent moiety and an acceptor fluorescent moiety. A representative donor fluorescent moiety is fluorescein, and representative corresponding acceptor fluorescent moieties include LC-Red 640, LC-Red 705, Cy5, and Cy5.5. Typically, detection includes exciting the sample at a wavelength absorbed by the donor fluorescent moiety and visualizing and/or measuring the wavelength emitted by the corresponding acceptor fluorescent moiety. In the process according to the invention, detection can be followed by quantitating the FRET. For example, detection is performed after each cycling step. For example, detection is performed in real time. By using commercially available real-time PCR instrumentation (e.g., LightCycler™ or TaqMan®), PCR amplification and detection of the amplification product can be combined in a single closed cuvette with dramatically reduced cycling time. Since detection occurs concurrently with amplification, the real-time PCR methods obviate the need for manipulation of the amplification product, and diminish the risk of cross-contamination between amplification products. Real-time PCR greatly reduces turn-around time and is an attractive alternative to conventional PCR techniques in the clinical laboratory.

The following patent applications describe real-time PCR as used in the LightCycler® technology: WO 97/46707, WO 97/46714 and WO 97/46712. The LightCycler® instrument is a rapid thermal cycler combined with a microvolume fluorometer utilizing high quality optics. This rapid thermocycling technique uses thin glass cuvettes as reaction vessels. Heating and cooling of the reaction chamber are controlled by alternating heated and ambient air. Due to the low mass of air and the high ratio of surface area to volume of the cuvettes, very rapid temperature exchange rates can be achieved within the thermal chamber.

TaqMan® technology utilizes a single-stranded hybridization probe labeled with two fluorescent moieties. When a first fluorescent moiety is excited with light of a suitable wavelength, the absorbed energy is transferred to a second fluorescent moiety according to the principles of FRET. The second fluorescent moiety is generally a quencher molecule. Typical fluorescent dyes used in this format are for example, among others, FAM, HEX, CY5, JA270, Cyan and CY5.5. During the annealing step of the PCR reaction, the labeled hybridization probe binds to the target nucleic acid (i.e., the amplification product) and is degraded by the 5' to 3'-exonuclease activity of the Taq or another suitable polymerase as known by the skilled artisan, such as a mutant Z05 polymerase, during the subsequent elongation phase. As a result, the excited fluorescent moiety and the quencher moiety become spatially separated from one another. As a consequence, upon excitation of the first fluorescent moiety in the absence of the quencher, the fluorescence emission from the first fluorescent moiety can be detected.

In both detection formats described above, the intensity of the emitted signal can be correlated with the number of original target nucleic acid molecules.

Recently, methods using "tagged" TaqMan® probes for performing multiplexed PCR assays have been described in U.S. Patent Publication No. 2018/0073056 and U.S. Patent Publication No. 2018/0073064, both incorporated by reference herein in their entireties.

As an alternative to FRET, an amplification product can be detected using a double-stranded DNA binding dye such as a fluorescent DNA binding dye (e.g., SYBRGREEN I® or SYBRGOLD® (Molecular Probes)). Upon interaction with the double-stranded nucleic acid, such fluorescent DNA binding dyes emit a fluorescence signal after excitation with light at a suitable wavelength. A double-stranded DNA binding dye such as a nucleic acid intercalating dye also can be used. When double-stranded DNA binding dyes are used, a melting curve analysis is usually performed for confirmation of the presence of the amplification product.

Molecular beacons in conjunction with FRET can also be used to detect the presence of an amplification product using the real-time PCR methods of the invention. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g. a hairpin). As a result of secondary structure formation within the probe, both fluorescent moieties are in spatial proximity when the probe is in solution. After hybridization to the amplification products, the secondary structure of the probe is disrupted and the fluorescent moieties become separated from one another such that after excitation with light of a suitable wavelength, the emission of the first fluorescent moiety can be detected.

Thus, a method according to the invention is the method described above using FRET, wherein said probes comprise a nucleic acid sequence that permits secondary structure formation, wherein said secondary structure formation results in spatial proximity between said first and second fluorescent moiety.

Efficient FRET can only take place when the fluorescent moieties are in direct local proximity and when the emission spectrum of the donor fluorescent moiety overlaps with the absorption spectrum of the acceptor fluorescent moiety.

Thus, in an embodiment, said donor and acceptor fluorescent moieties are within no more than five nucleotides of each other on said probe. In a further embodiment, said acceptor fluorescent moiety is a quencher.

As described above, in the TaqMan® format, during the annealing step of the PCR reaction, the labeled hybridization probe binds to the target nucleic acid (i.e., the amplification product) and is degraded by the 5'- to 3'-exonuclease activity of the Taq or another suitable polymerase as known by the skilled artisan, such as a mutant Z05 polymerase, during the subsequent elongation phase. Thus, in an embodiment, in the process described above, amplification employs a polymerase enzyme having 5'- to 3'-exonuclease activity.

It is further advantageous to carefully select the length of the amplicon that is yielded as a result of the process described above. Generally, relatively short amplicons increase the efficiency of the amplification reaction. Thus, an aspect of the invention is the process described above, wherein the amplified fragments comprise up to 450 bases, up to 300 bases, up to 200 bases, or up to 150 bases.

A "sequence" is the primary structure of a nucleic acid, i.e. the specific arrangement of the single nucleobases of which the respective nucleic acids consists. It has to be understood that the term "sequence" does not denote a specific type of nucleic acid such as RNA or DNA, but applies to both as well as to other types of nucleic acids such as e.g. PNA or others. Where nucleobases correspond to each other, particularly in the case of uracil (present in RNA) and thymine (present in DNA), these bases can be considered equivalent between RNA and DNA sequences, as well-known in the pertinent art.

Clinically relevant nucleic acids are often DNA which can be derived e.g. from DNA viruses like e.g. Hepatitis B Virus (HBV), Cytomegalovirus (CMV) and others, or bacteria like e.g. *Chlamydia trachomatis* (CT), *Neisseria gonorrhoeae* (NG) and others. In such cases, it can be advantageous to use an internal control nucleic acid consisting of DNA, in order to reflect the target nucleic acids properties. The terms "cell", "cell line", and "cell culture" can be used interchangeably and all such designations include progeny. Thus, the words "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants. The cells can be prokaryotic or eukaryotic.

The term "control sequences" refers to DNA sequences necessary for the expression of an operably linked coding sequence in a particular host organism. The control sequences that are suitable for prokaryotes, for example, include a promoter, optionally an operator sequence, a ribosome binding site, positive retroregulatory elements (see U.S. Pat. No. 4,666,848, incorporated herein by reference), and possibly other sequences. Eukaryotic cells are known to utilize promoters, polyadenylation signals, and enhancers.

The term "operably linked" refers to the positioning of the coding sequence such that control sequences will function to drive expression of the protein encoded by the coding sequence. Thus, a coding sequence "operably linked" to control sequences refers to a configuration wherein the coding sequences can be expressed under the direction of a control sequence.

The terms "restriction endonucleases" and "restriction enzymes" refer to enzymes, typically bacterial in origin, which cut double-stranded DNA at or near a specific nucleotide sequence.

Families of amino acid residues having similar side chains are defined herein. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine), nonpolar side chains (e.g., alanine, valine, leucine, isoleucine, proline, phenylalanine, methionine, tryptophan, cysteine, glycine), β-branched side chains (e.g., threonine, valine, isoleucine) and aromatic side chains (e.g., tyrosine, phenylalanine, tryptophan, histidine).

The term "reagent solution" is any solution containing at least one reagent needed or used for PCR purposes. Most typical ingredients are polymerase, nucleotide, primer, ions, magnesium, salts, pH buffering agents, nucleoside triphosphates (NTPs) or deoxyribonucleoside triphosphates (dNTPs), probe, fluorescent dye (may be attached to probe), nucleic acid binding agent, a nucleic acid template. The reagent may also be other polymerase reaction additive, which has an influence on the polymerase reaction or its monitoring.

The term "master mix" refers to a mixture of all or most of the ingredients or factors necessary for PCR to occur, and in some cases, all except for the template and primers which are sample and amplicon specific. Commercially available master mixes are usually concentrated solutions. A master mix may contain all the reagents common to multiple samples, but it may also be constructed for one sample only. Using master mixes helps to reduce pipetting errors and variations between samples due to differences between pipetted volumes.

The term "thermostable polymerase" refers to an enzyme that is stable to heat, is heat resistant and retains sufficient activity to effect subsequent primer extension reactions after being subjected to the elevated temperatures for the time necessary to denature double-stranded nucleic acids. Heating conditions necessary for nucleic acid denaturation are well known in the art and are exemplified in U.S. Pat. Nos. 4,965,188 and 4,889,818, which are incorporated herein by reference. As used herein, a thermostable polymerase is suitable for use in a temperature cycling reaction such as PCR. The examples of thermostable nucleic acid polymerases include *Thermus aquaticus* Taq DNA polymerase, *Thermus* sp. Z05 polymerase, *Thermus flavus* polymerase, *Thermotoga maritima* polymerases, such as TMA-25 and TMA-30 polymerases, Tth DNA polymerase, and the like.

A "polymerase with reverse transcriptase activity" is a nucleic acid polymerase capable of synthesizing DNA based on an RNA template. It is also capable of replicating a single or double-stranded DNA once the RNA has been reverse transcribed into a single strand cDNA. In an embodiment of the invention, the polymerase with reverse transcriptase activity is thermostable.

In the amplification of an RNA molecule by a DNA polymerase, the first extension reaction is reverse transcription using an RNA template, and a DNA strand is produced. The second extension reaction, using the DNA template, produces a double-stranded DNA molecule. Thus, synthesis of a complementary DNA strand from an RNA template by a DNA polymerase provides the starting material for amplification.

Thermostable DNA polymerases can be used in a coupled, one-enzyme reverse transcription/amplification reaction. The term "homogeneous", in this context, refers to a two-step single addition reaction for reverse transcription and amplification of an RNA target. By homogeneous it is meant that following the reverse transcription (RT) step, there is no need to open the reaction vessel or otherwise adjust reaction components prior to the amplification step. In a non-homogeneous RT-PCR reaction, following reverse transcription and prior to amplification one or more of the reaction components such as the amplification reagents are e.g. adjusted, added, or diluted, for which the reaction vessel has to be opened, or at least its contents have to be manipulated. Both homogeneous and non-homogeneous embodiments are comprised by the scope of the invention.

Reverse transcription is an important step in an RT-PCR. It is, for example, known in the art that RNA templates show a tendency towards the formation of secondary structures that may hamper primer binding and/or elongation of the cDNA strand by the respective reverse transcriptase. Thus, relatively high temperatures for an RT reaction are advantageous with respect to efficiency of the transcription. On the other hand, raising the incubation temperature also implies higher specificity, i.e. the RT primers will not anneal to sequences that exhibit mismatches to the expected sequence or sequences. Particularly in the case of multiple different target RNAs, it can be desirable to also transcribe and subsequently amplify and detect sequences with single mismatches, e.g. in the case of the possible presence of unknown or rare substrains or subspecies of organisms in the fluid sample.

In order to benefit from both advantages described above, i.e. the reduction of secondary structures and the reverse transcription of templates with mismatches, the RT incubation can be carried out at more than one different temperature.

Therefore, an aspect of the invention is the process described above, wherein said incubation of the polymerase with reverse transcriptase activity is carried out at different temperatures from 30° C. to 75° C., or from 45° C. to 70° C., or from 55° C. to 65° C.

As a further important aspect of reverse transcription, long RT steps can damage the DNA templates that may be present in the fluid sample. If the fluid sample contains both RNA and DNA species, it is thus favorable to keep the duration of the RT steps as short as possible, but at the same time ensuring the synthesis of sufficient amounts of cDNA for the subsequent amplification and optional detection of amplification products.

Thus, an aspect of the invention is the process described above, wherein the period of time for incubation of the polymerase with reverse transcriptase activity is up to 30 min., 20 min., 15 min., 12.5 min., 10 min., 5 min., or 1 min.

A further aspect of the invention is the process described above, wherein the polymerase with reverse transcriptase activity and comprising a mutation is selected from the group consisting of a) a CS5 DNA polymerase
b) a CS6 DNA polymerase
c) a *Thermotoga maritima* DNA polymerase
d) a *Thermus aquaticus* DNA polymerase
e) a *Thermus thermophilus* DNA polymerase
f) a *Thermus flavus* DNA polymerase
g) a *Thermus filiformis* DNA polymerase
h) a *Thermus* sp. sps17 DNA polymerase
i) a *Thermus* sp. Z05 DNA polymerase
j) a *Thermotoga neapolitana* DNA polymerase
k) a *Thermosipho africanus* DNA polymerase
l) a *Thermus caldophilus* DNA polymerase Particularly suitable for these requirements are enzymes carrying a mutation in the polymerase domain that enhances their reverse transcription efficiency in terms of a faster extension rate.

Therefore, in the process described above, wherein the polymerase with reverse transcriptase activity is a polymerase comprising a mutation conferring an improved nucleic acid extension rate and/or an improved reverse transcriptase activity relative to the respective wild-type polymerase.

In an embodiment, in the process described above, the polymerase with reverse transcriptase activity is a polymerase comprising a mutation conferring an improved reverse transcriptase activity relative to the respective wild-type polymerase.

Polymerases carrying point mutations that render them particularly useful are disclosed in WO 2008/046612. In particular, polymerases to be used can be mutated DNA polymerases comprising at least the following motif in the polymerase domain:

T-G-R-L-S-S-Xb7-Xb8-P-N-L-Q-N; wherein Xb7 is an amino acid selected from S or T and wherein Xb8 is an amino acid selected from G, T, R, K, or L, wherein the polymerase comprises 3'-5' exonuclease activity and has an improved nucleic acid extension rate and/or an improved reverse transcription efficiency relative to the wild-type DNA polymerase, wherein in said wild-type DNA polymerase Xb8 is an amino acid selected from D, E or N.

One example is mutants of the thermostable DNA polymerase from *Thermus* species Z05 (described e.g. in U.S. Pat. No. 5,455,170), said variations comprising mutations in the polymerase domain as compared with the respective wild-type enzyme Z05. An embodiment for the method according to the invention is a mutant Z05 DNA polymerase wherein the amino acid at position 580 is selected from the group consisting of G, T, R, K and L.

For reverse transcription using a thermostable polymerase, a divalent cation such as $Mn^{2+}$ or $Mg^{2+}$ is typically included as a salt, for example, manganese chloride ($MnCl_2$), manganese acetate ($Mn(OAc)_2$), or manganese sulfate ($MnSO_4$) or magnesium chloride ($MgCl_2$), magnesium acetate ($Mg(OAc)_2$), or magnesium sulfate ($MgSO_4$). If $MnCl_2$ is included in a reaction containing 50 mM Tricine buffer, for example, the $MnCl_2$ is generally present at a concentration of 0.5-7.0 mM; 2.5-3.5 mM is generally present when 200 μM of each dGTP, dATP, dUTP, and, dCTP are utilized.

A "modified" thermostable polymerase refers to a polymerase in which at least one monomer differs from the reference sequence, such as a native or wild-type form of the polymerase or another modified form of the polymerase. Exemplary modifications include monomer insertions, deletions, and substitutions. Modified polymerases also include chimeric polymerases that have identifiable component sequences (e.g., structural or functional domains, etc.) derived from two or more parents. Also included within the definition of modified polymerases are those comprising chemical modifications of the reference sequence. The examples of modified thermostable polymerases include G46E E678G CS5 DNA polymerase, G46E L329A E678G CS5 DNA polymerase, G46E L329A D640G S671F CS5 DNA polymerase, G46E L329A D640G S671F E678G CS5 DNA polymerase, a G46E E678G CS6 DNA polymerase, Z05 DNA polymerase, ΔZ05 polymerase, ΔZ05-Gold polymerase, ΔZ05R polymerase, E615G Taq DNA polymerase, E678G TMA-25 polymerase, E678G TMA-30 polymerase, and the like.

The term "thermoactive polymerase" refers to an enzyme that is active at the elevated temperatures necessary to ensure specific priming and primer extension (e.g., 55-80° C.).

The terms "peptide," "polypeptide," and "protein" are used interchangeably. The terms "nucleic acid" and "polynucleotide" are used interchangeably. Amino acid sequences are written from amino-terminus to carboxy-terminus, unless otherwise indicated. Single-stranded nucleic acid sequences are written 5' to 3', unless otherwise indicated. The top strand of a double-stranded nucleic acid sequence is written 5' to 3', and the bottom strand is written 3' to 5', unless otherwise indicated.

While the foregoing invention has been described in some detail for purposes of clarity and understanding, it will be clear to one skilled in the art from a reading of this disclosure that various changes in form and detail can be made without departing from the true scope of the invention. For example, all the compositions and methods described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

Chemical structures of compounds disclosed in the present application are numbered and shown as follows:

Silicon and germanium anilines/azetidines

| Compound No. | Chemical structure |
| --- | --- |
| 1 | 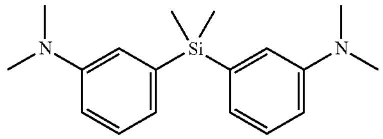 |
| 2 | 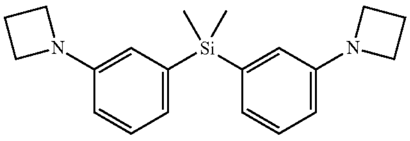 [SMILES: C[Si](C)(c1cccc(N2CCC2)c1)c1cccc(N2CCC2)c1] |
| 3 | 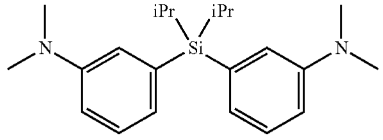 |
| 4 | 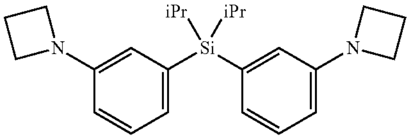 [SMILES: CC(C)[Si](c1cccc(N2CCC2)c1)(c1cccc(N2CCC2)c1)C(C)C] |
| 5 | 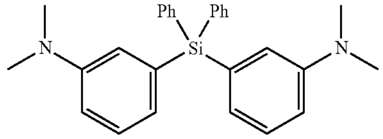 |
| 6 | 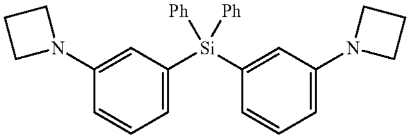 [SMILES: c1ccc([Si](c2ccccc2)(c2cccc(N3CCC3)c2)c2cccc(N3CCC3)c2)cc1] |
| 7 | 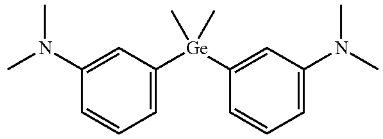 |
| 8 | 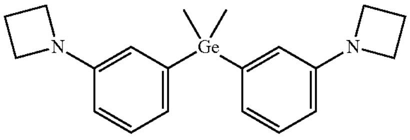 |

-continued
| Silicon and germanium anilines/azetidines | |
|---|---|
| Compound No. | Chemical structure |
| 9 | 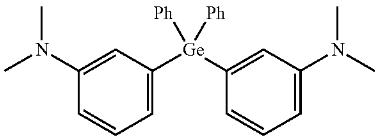 |
| 10 | 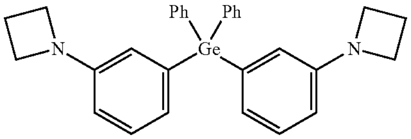 |
| Dibromides | |
|---|---|
| Compound No. | Chemical structure |
| 11 | 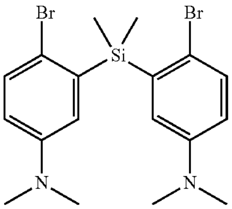 [SMILES: CN(C)c1ccc(Br)c([Si](C)(C)c2cc(N(C)C)ccc2Br)c1] |
| 12 | 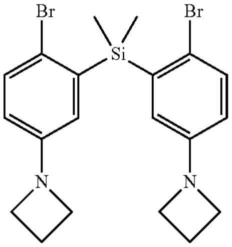 [SMILES: C[Si](C)(c1cc(N2CCC2)ccc1Br)c1cc(N2CCC2)ccc1Br] |
| 13 | 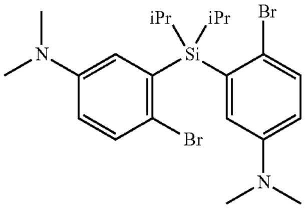 |
| 14 | 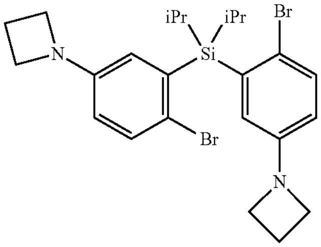 [SMILES: CC(C)[Si](c1cc(N2CCC2)ccc1Br)(c1cc(N2CCC2)ccc1Br)C(C)C] |
-continued
| Dibromides | |
|---|---|
| Compound No. | Chemical structure |
| 15 | 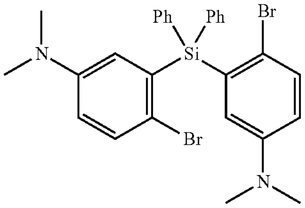 |
| 16 | 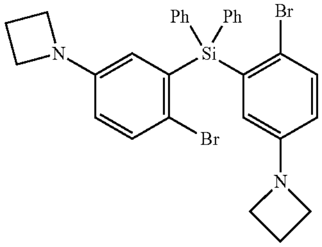 [SMILES: Brc1ccc(N2CCC2)cc1[Si](c1ccccc1)(c1ccccc1)c1cc(N2CCC2)ccc1Br] |
| 17 | 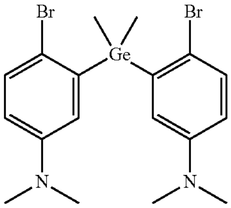 |
| 18 | 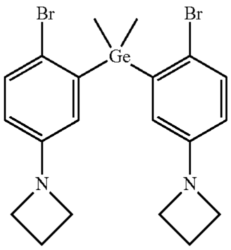 |
| 19 | 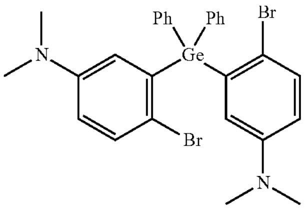 |
| 20 | 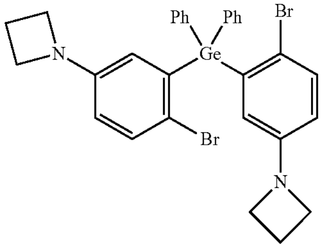 |

| Imidazoles | |
|---|---|
| Compound No. | Chemical structure |
| 21 | 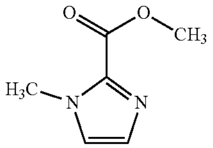 |
| 22 | 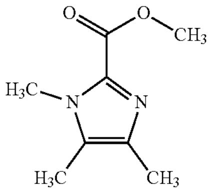 |
| 23 | 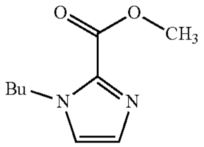 |
| Imidazole dyes | |
|---|---|
| Compound No. | Chemical structure |
| 24 | 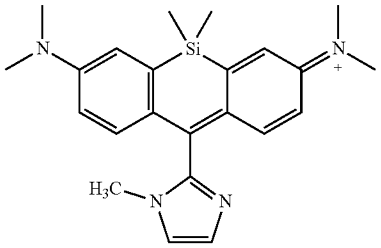 |
-continued
| Imidazole dyes | |
|---|---|
| Compound No. | Chemical structure |
| 25 | 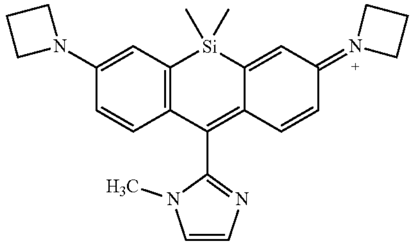 |
| 26 | 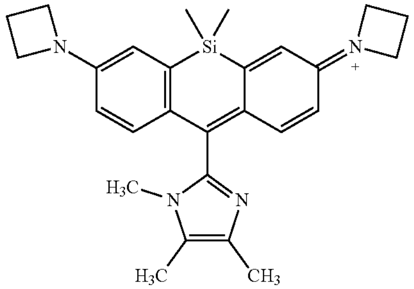 |
| 27 | 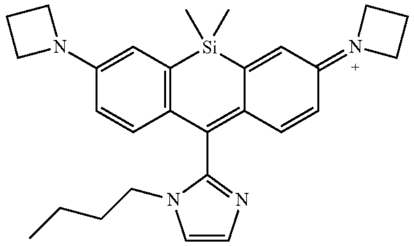 |
| 28 | 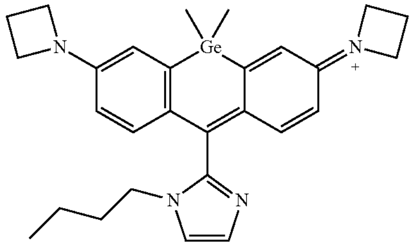 |
| Imidazolium dyes | |
|---|---|
| Compound No. | Chemical structure |
| 29 | 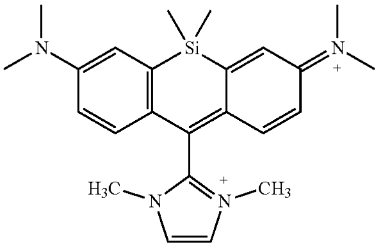 |

-continued
| Imidazolium dyes | |
|---|---|
| Compound No. | Chemical structure |
| 30 | 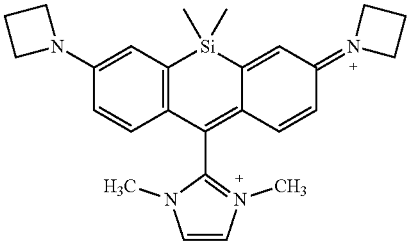 |
| 31 | 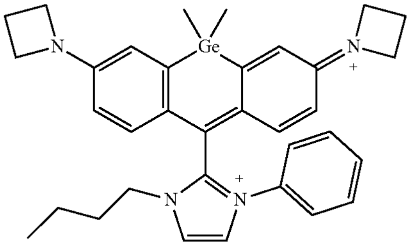 |
| 32 | 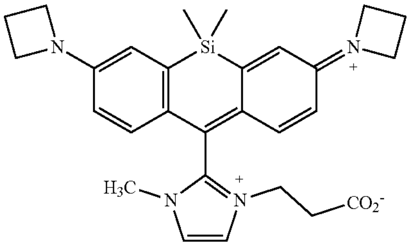 |
| 33 | 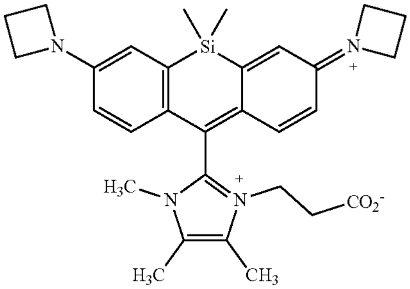 |
| 34 | 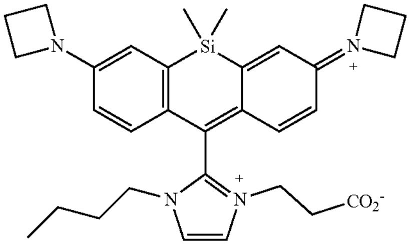 |

-continued

| Imidazolium dyes | |
|---|---|
| Compound No. | Chemical structure |
| 35 | 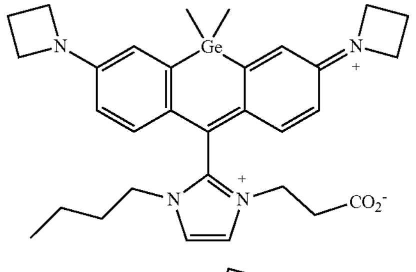 |
| 36 | 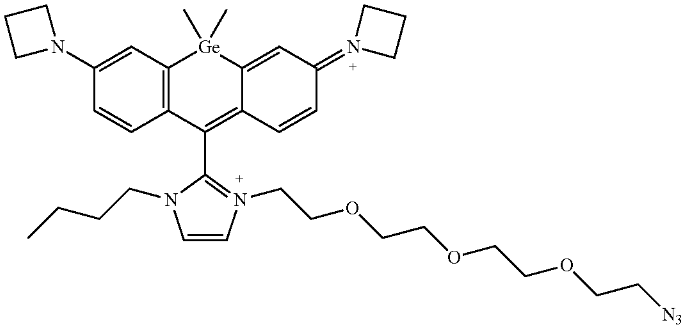 |

EXAMPLES

The following examples are given to illustrate embodiments of the present invention as it is presently preferred to practice. It will be understood that the examples are illustrative, and that the invention is not be considered as restricted except as indicated in the appended claims.

Abbreviations: abs.=absolute, AcOH=acetic acid, aq.=aqueous, dATP=2'-deoxyadenosine 5'-triphosphate, dCTP=2'-deoxycytidine 5'-triphosphate, dGTP=2'-deoxyguanosine 5'-triphosphate, DBCO=dibenzocyclooctyne modification; DCM=dichloromethane, DMF=N,N'-dimethylformamide, DMSO=dimethyl sulfoxide, dUTP=2'-deoxyuridine 5'-triphosphate, eq.=molar equivalents, $Et_2O$=diethyl ether, EtOAc=ethyl acetate, MeCN=acetonitrile, MeOH=methanol, qPCR=real-time polymerase chain reaction, RT=room temperature, SPE=solid-phase extraction, TBAF=tetrabutylammonium fluoride, THF=tetrahydrofuran, TLC=thin-layer chromatography, UPLC-MS=ultra-performance liquid chromatography coupled to a mass spectrometer.

General Materials and Methods

Reagents were obtained from MilliporeSigma (Burlington, MA, U.S.A.) unless stated otherwise. tert-Butyllithium solution (1.5 M in n-pentane) was obtained from Alfa Aesar (Haverhill, MA, U.S.A.). 1-(3-Bromophenyl)azetidine and methyl 1-butyl-1H-imidazole-2-carboxylate were obtained from ChemShuttle (Hayward, CA, U.S.A.). Methyl 1-methyl-1H-imidazole-2-carboxylate was obtained from AA Blocks LLC (San Diego, CA, U.S.A.). Methyl 1,4,5-trimethyl-1H-imidazole-2-carboxylate was obtained from ChemSpace (Monmouth Junction, NJ, U.S.A.). 2-(Trimethylsilyl)phenyl trifluoromethanesulfonate was obtained from TCI America (Portland, Oregon, U.S.A.). 1-azido-2-(2-(2-(2-bromoethoxy) ethoxy) ethoxy) ethane (bromo-PEG3-azide) was obtained from BroadPharm (San Diego, CA, U.S.A.). Reagents and materials for chemical DNA synthesis were obtained from Glen Research (Sterling, VA, U.S.A.).

All synthetic transformations were carried out under dry argon atmosphere with flame-dried glassware unless stated otherwise. Solvents for chemical reactions were obtained from Acros Organics (Thermo Fisher Scientific, Waltham, MA, U.S.A.) and stored over activated molecular sieves. Solvents for chromatography (HPLC grade) were obtained from MilliporeSigma or VWR (Radnor, PA, U.S.A.) and used without further purification. Microwave assisted reactions were performed with a Discover® SP microwave system from CEM (Matthews, NC, USA), equipped with a focused single-mode reaction chamber (2.45 GHz) in heavy-walled glass vials (2.0 mL or 10.0 mL). The reaction temperature was monitored with a built-in IR temperature sensor and kept constant by automatic power control. Microwave assisted reactions were stirred under active cooling with compressed air. Flash column chromatography was performed with an automated flash chromatography system (CombiFlash® Rf+ Lumen) from Teledyne-Isco (Lincoln, NE, U.S.A.). UPLC analysis was performed on a Waters I-class ACQUITY UPLC (Waters Corporation, Milford, MA, USA) equipped with diode array, fluorescence, and mass spectrometry (ZSpraym) detectors. A Waters Oligonucleotide BEH C18 column (130 Å, 1.7 μm, 2.1×50 mm) was used with appropriate gradients of TEAA buffer (100 mM, pH 7.0) or $H_2O$ (0.1% formic acid) against MeCN at 1.0 ml/min. Semi-preparative HPLC purifications were performed on a Waters 600 HPLC with 996 photodiode array detector and Waters XBridge™ BEH C18 OBD Prep column (130 Å, 5 μm, 19.0×250 mm) at 10.0 ml/min. Prior to injection the samples were filtered through a Teflon syringe filter (0.20 μm). Absorption spectra were obtained with an Agilent 8453 UV-visible spectrophotometer (Santa Clara, CA, U.S.A.). Fluorescence spectra were recorded with an Agilent Cary Eclipse fluorescence spectrophotometer.

Compounds with one or more positive charges (24-36) were obtained as acetate, chloride, bromide, or iodide salts, depending on the respective work-up or purification method. Replacement of the counterion was achieved by standard ion exchange procedures using a suitable ion-exchange resin, liquid-liquid extraction, or precipitation from organic solvent.

Example 1: Reaction Scheme General Procedure

Figure 5:
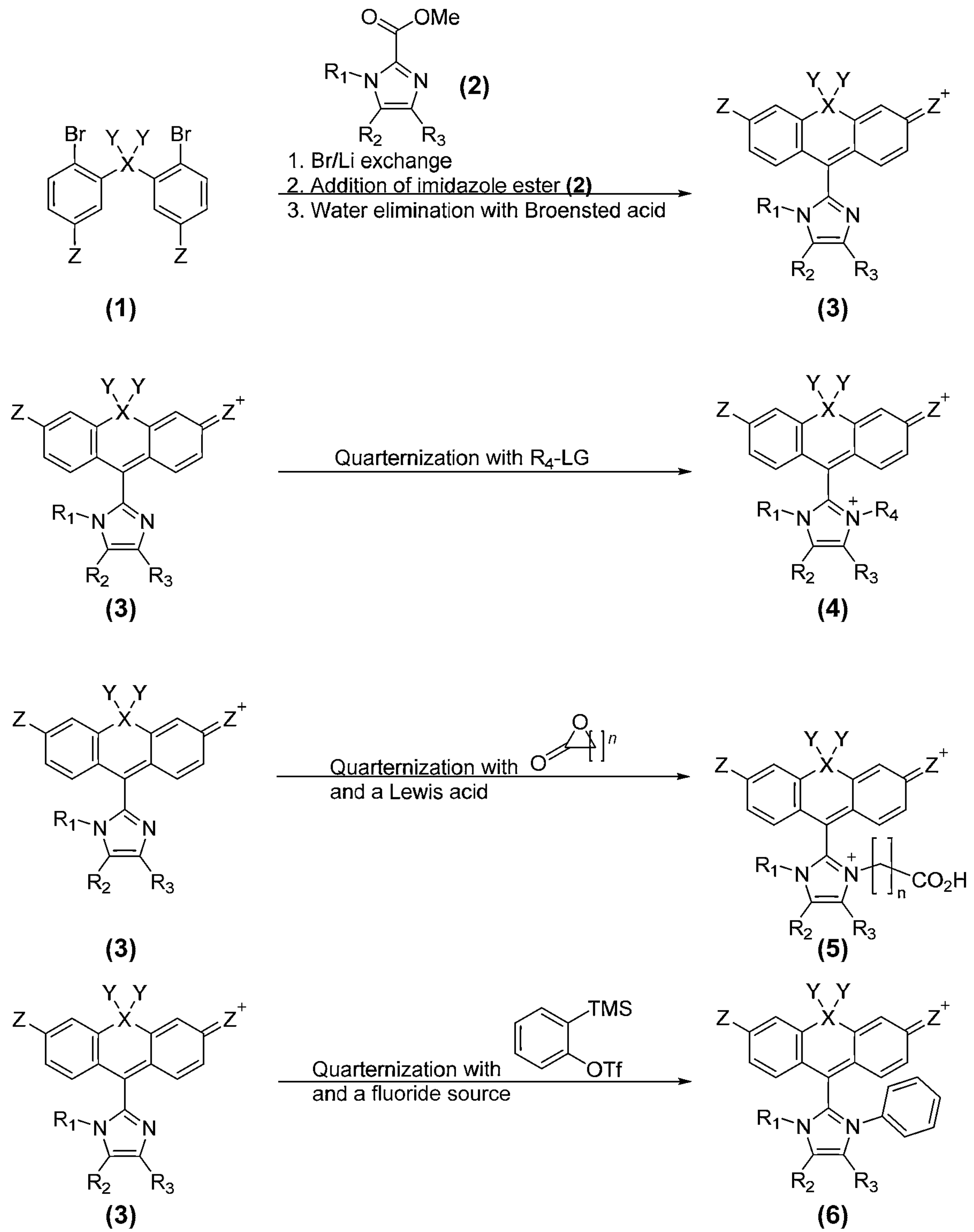
FIG. 5: Shows a general reaction scheme for synthesizing the fluorescent dyes according to the disclosure.

A general reaction scheme for preparing the fluorescent dyes according to the disclosure is provided in FIG. 5. As laid out in the figure, the method for preparing the fluorescent dyes comprises the step of dye core formation. Herein, a double halogen-metal exchange of the dihalogenide (1) to the corresponding dilithium compound with an organolithium reagent is performed, which for example can be tert-butyllithium. Subsequently, the intermediate ("in situ") is reacted with an alkylester, for example a methyl ester of 1-alkyl- or 1-aryl-1H-imidazole-2-carboxylate (2). Subsequently, an aromatization is performed by elimination of water from the hydroxyl-intermediate by addition of a Brønsted acid ("one-pot reaction"), for example acetic acid, to receive compound (3). The dye core formation reaction is followed by quarternization of the imidazole to imidazolium. In some aspects, quarternization of the imidazole (3) to the imidazolium compound is performed by nucleophilic substitution with an alkylhalogenide, alkyltosylate, alkyltriflate, or alkylmesylate, to receive the alkylated compound (4). In other aspects, quarternization of the imidazole (3) to the imidazolium compound is performed with a cyclic lactone, for example beta-propiolactone, in the presence of a Lewis acid, for example aluminium tribromide, to receive the carboxylic acid (5). In yet other aspects, quarternization of the 3-imidazole nitrogen (3) to the imidazolium compound with in situ generated aryne from a 2-(trimethylsilyl) phenyl trifluoromethanesulfonate reagent and a fluoride donor is performed, which for example is tetrabutylammonium fluoride or tetrabutylammonium difluorotriphenylsilicate, to receive the arylated compound (6).

Example 2: General Procedure to Synthesize Compounds 1-10

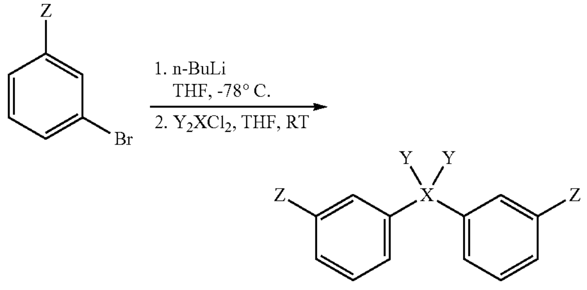

with X=Si, Ge; Y=Me, iPr, Ph; Z=$NMe_2$, $NC_3H_6$.

Compounds 1-10 [3,3'-(dimethylsilanediyl)bis(N,N-dimethylaniline) 1, bis(3-(azetidin-1-yl)phenyl)dimethylsilane 2, 3,3'-(diisopropylsilanediyl)bis(N,N-dimethylaniline) 3, bis(3-(azetidin-1-yl)phenyl)diisopropylsilane 4, 3,3'-(diphenylsilanediyl)bis(N,N-dimethylaniline) 5, bis(3-(azetidin-1-yl)phenyl)diphenylsilane 6, 3,3'-(dimethylgermanediyl)bis(N,N-dimethyl aniline) 7, bis(3-(azetidin-1-yl)phenyl) dimethylgermane 8, 3,3'-(diphenylgermanediyl)bis(N,N-dimethylaniline) 9, bis(3-(azetidin-1-yl)phenyl) diphenylgermane 10] were synthesized starting from 3-bromo-N,N-dimethylaniline or 1-(3-bromophenyl)azetidine and the respective silane or germane reagent, which was selected from dichlorodimethylsilane, dichlorodiisopropylsilane, dichlorodiphenylsilane, dimethylgermanium dichloride, or diphenylgermanium dichloride.

A solution of 3-bromo-N,N-dimethylaniline or 1-(3-bromophenyl)azetidine (2.4 eq.) in dry THF (17.0 mL) was cooled to −78° C., followed by slow and dropwise addition of n-butyllithium solution (2.4 eq., 2.5 M in hexanes). The reaction was stirred at −78° C. for 0.5 h. At the same temperature a solution of the respective silane or germane (1.0 eq., 4.0 mmol) in THF (2.2 mL) was added. Subsequently, the cooling bath was removed and the reaction mixture was stirred at RT for 3 h, or until TLC analysis (silica, EtOAc/hexanes) showed complete conversion of the starting material. The reaction was quenched with saturated aq. $NH_4Cl$ (5.0 mL), diluted with $H_2O$ (20 mL), and extracted with EtOAc. The combined organic layers were washed with brine, dried over anhydrous $MgSO_4$, and filtered. The solvent was evaporated and the residue dried under high vacuum. Purification of the raw product by flash chromatography on silica (silica, 0-10% EtOAc in hexanes) afforded the title compound as colorless oil. The identity of the products was confirmed by NMR and UPLC-MS analysis ($C_{18}$, $H_2O$, 0.1% formic acid, 50-100% MeCN in 2.0 min.).

Example 3: General Procedure to Synthesize Compounds 11-20

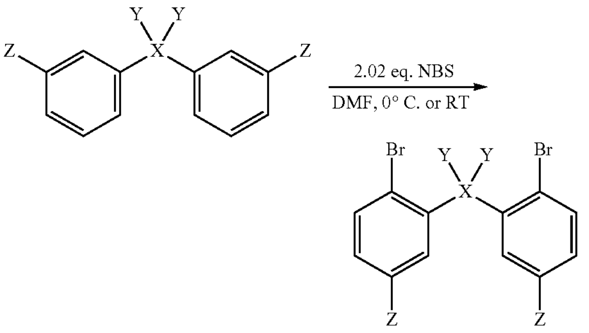

with X=Si, Ge; Y=Me, iPr, Ph; Z=$NMe_2$, $NC_3H_6$.

Compounds 11-20 [3,3'-(dimethylsilanediyl)bis(4-bromo-N,N-dimethylaniline) 11, bis(5-(azetidin-1-yl)-2-bromophenyl)dimethylsilane 12, 3,3'-(diisopropylsilanediyl)bis(4-bromo-N,N-dimethylaniline) 13, bis(5-(azetidin-1-yl)-2-bromophenyl)diisopropylsilane 14, 3,3'-(diphenylsilanediyl)bis(4-bromo-N,N-dimethylaniline) 15, bis(5-(azetidin-1-yl)-2-bromophenyl)diphenylsilane 16, 3,3'-(dimethylgermanediyl)bis(4-bromo-N,N-dimethyl-aniline) 17, bis(5-(azetidin-1-yl)-2-bromophenyl)dimethylgermane 18, 3,3'-(diphenylgermanediyl)bis(4-bromo-N,N-dimethylaniline) 19, bis(5-(azetidin-1-yl)-2-bromophenyl) diphenylgermane 20] were synthesized from compounds 1-10.

The aniline or azetidine (1.0 eq., 3.0 mmol) was dissolved in dry DMF (18.9 mL) and cooled with an ice bath. While stirring N-bromosuccinimide (2.02 eq.) was added over a period of 0.5 h. The reaction was stirred at room temperature for 3 h or until TLC analysis (silica, EtOAc/hexanes) showed complete conversion of the starting material. The mixture was diluted with DCM and extracted twice with half-saturated aq. $NaHCO_3$. The organic layer was washed with saturated aq. NaCl, dried with $MgSO_4$, and filtered. The solvent was evaporated and the residue dried under high vacuum. Pure product was obtained by flash chromatography (silica, 0-10% EtOAc in hexanes) or recrystallization. The identity of the product was confirmed by NMR and UPLC-MS analysis ($C_{18}$, $H_2O$, 0.1% formic acid, 50-100% MeCN in 2.0 min.).

Example 4: General Procedure to Synthesize Dyes 24-28

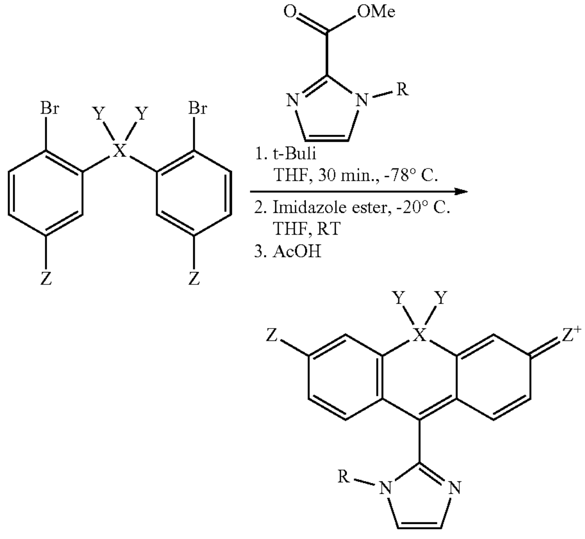

with X=Si, Ge; Y=Me, iPr, Ph; Z=$NMe_2$, $NC_3H_6$; R=Me, Bu.

Dyes 24-28 were synthesized from compounds 11, 12, 20 and the respective imidazole methyl ester 21-23 [methyl 1-methyl-1H-imidazole-2-carboxylate 21, methyl 1,4,5-trimethyl-1H-imidazole-2-carboxylate 22, methyl 1-butyl-1H-imidazole-2-carboxylate 23].

A solution of the respective dibromide (1.0 eq., 450 μmol) in abs. THF (5.75 mL) was cooled to −78° C. tert-Butyllithium solution (4.4 eq., 1.5 M in n-pentane) was added dropwise and the reaction was stirred at −78° C. for 30 min. The temperature of the reaction was raised to −20° C., followed by slow addition of a solution of the respective imidazole methyl ester (2.2 eq.) in abs. THF (5.75 mL) over 0.5 h. The mixture was stirred 18 h at RT. The pH of the reaction mixture was set to 4.0 with glacial acetic acid and the solution was stirred 4 h at RT during which strong blue coloration occurred. The reaction mixture was extracted with saturated aq. KBr and DCM. The combined organic layers were washed with $H_2O$, dried over $Na_2SO_4$ and filtered. The solvent was evaporated under reduced pressure. The residue was redissolved in a minimum amount of DCM and added to a stirring solution of $Et_2O$. A blue precipitate formed that was isolated and washed by centrifugation. The yellow-colored supernatant was discarded. The dark blue dye was dried at high vacuum and purified by semi-preparative HPLC ($C_{18}$, TEAA/MeCN).

Example 5: General Procedure to Synthesize Dyes 29 and 30

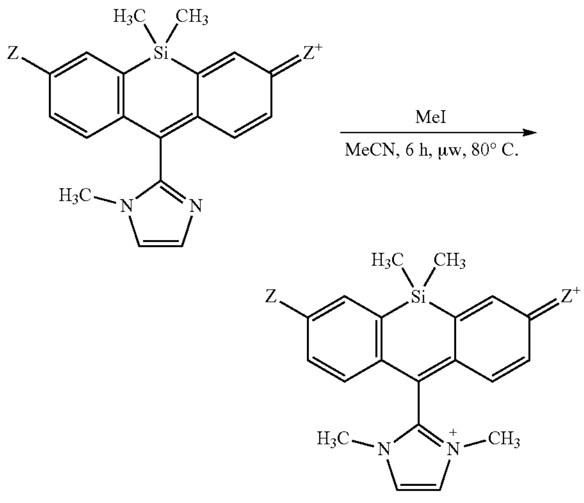

with Z=$NMe_2$, $NC_3H_6$.

The imidazolium dyes 29 and 30 were synthesized from dyes 24 and 25, respectively.

A solution of imidazole dye (1.0 eq., 17 μmol) and methyl iodide (2.0 eq.) in MeCN was heated to 80° C. by microwave irradiation for 6 h. The reaction mixture was added to stirring $Et_2O$. The precipitate was isolated by centrifugation and the supernatant discarded. Finally, the crude product was purified by semi-preparative HPLC ($C_{18}$, TEAA/MeCN). Fluorescence spectra and temperature dependence of fluorescence are shown in FIG. 1.

Example 6: Procedure to Synthesize Dye 31

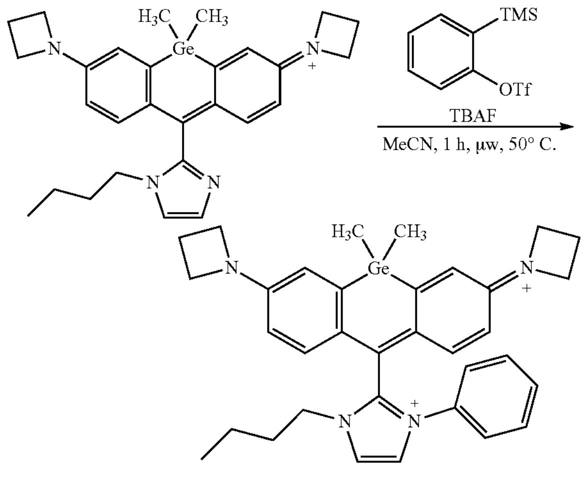

A solution of the imidazole dye (1.0 eq., 17 μmol, 30 mM final) and 2-(trimethylsilyl)phenyl trifluoromethanesulfonate (5.0 eq.) in abs. MeCN was prepared, and dry TBAF (1.0 M in THF, 5.0 eq.) was added last to start the reaction. The stirring solution was heated by microwave irradiation at 50° C. for 1.0 h. UPLC-MS analysis (30-60% MeCN in 2 min.) confirmed that the reaction was complete. The mixture was poured to stirring $Et_2O$, to which solid NaI (2.0 eq.) was added. A precipitate formed which was isolated by centrifugation. The supernatant was discarded and the residue was taken up in $H_2O$. Insoluble by-products were removed with a Teflon syringe filter and the imidazolium dye was obtained from the supernatant by semi-preparative HPLC ($C_{18}$, TEAA, 30-60% MeCN).

Example 7: General Procedure to Synthesize Dyes 32-35

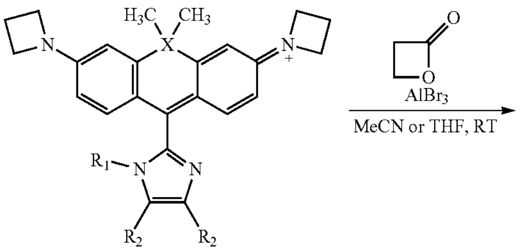

-continued

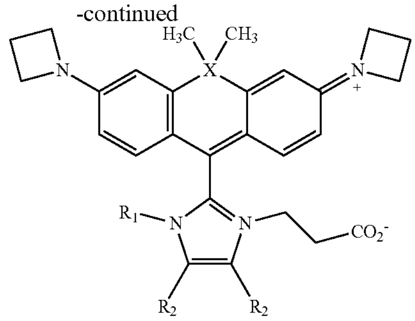

with X=Si, Ge; $R_1$=Me, Bu, $R_2$=H, Me.

A solution of the imidazole dye (1.0 eq., 20 μmol, 78 mM final) and β-propiolactone (10.0 eq.) in abs. MeCN was prepared, and $AlBr_3$ was added last to start the reaction. The solution was stirred for 1.0 h at RT during which some precipitate formed. UPLC-MS analysis (30-60% MeCN in 2 min.) confirmed that the reaction was complete. The mixture was poured to stirring $Et_2O$. A precipitate formed which was isolated by centrifugation. The residue was washed with $Et_2O$, dried at high vacuum and redissolved in MeCN (400 μL). TEAA buffer (3.6 mL) was added and insoluble by-products were removed with a Teflon syringe filter. The imidazolium dye was obtained from the supernatant by semi-preparative HPLC ($C_{18}$, TEAA, 30-60% MeCN).

Example 8: Procedure to Synthesize Dye 36

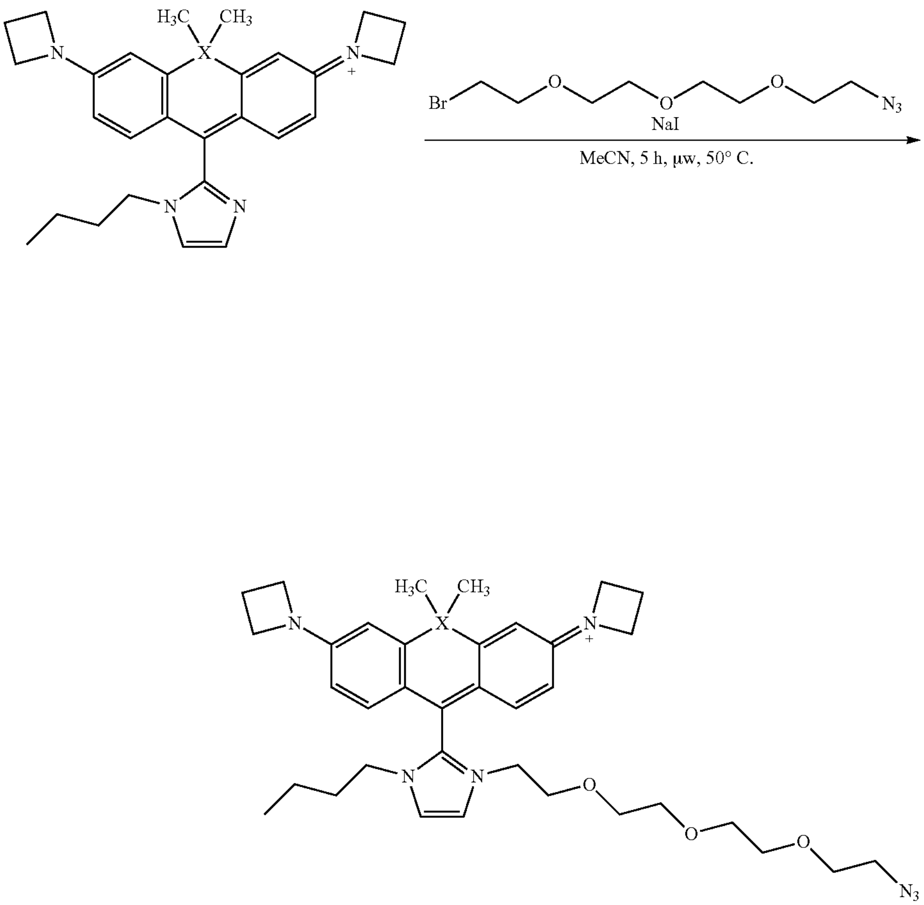

A solution of the imidazole dye (1.0 eq., 17 μmol, 50 mM final) and bromo-PEG3-azide (2.0 eq.), and NaI (10.0 eq.) in abs. MeCN was heated at 50° C. for 12 h by microwave irradiation. The product was precipitated from $Et_2O$ and purified by semi-preparative HPLC ($C_{18}$, TEAA, 25%-45% MeCN). The purified product was desalted by SPE.

Example 9: Preparation of Dye Labeled DNA Probes

Figure 2A:
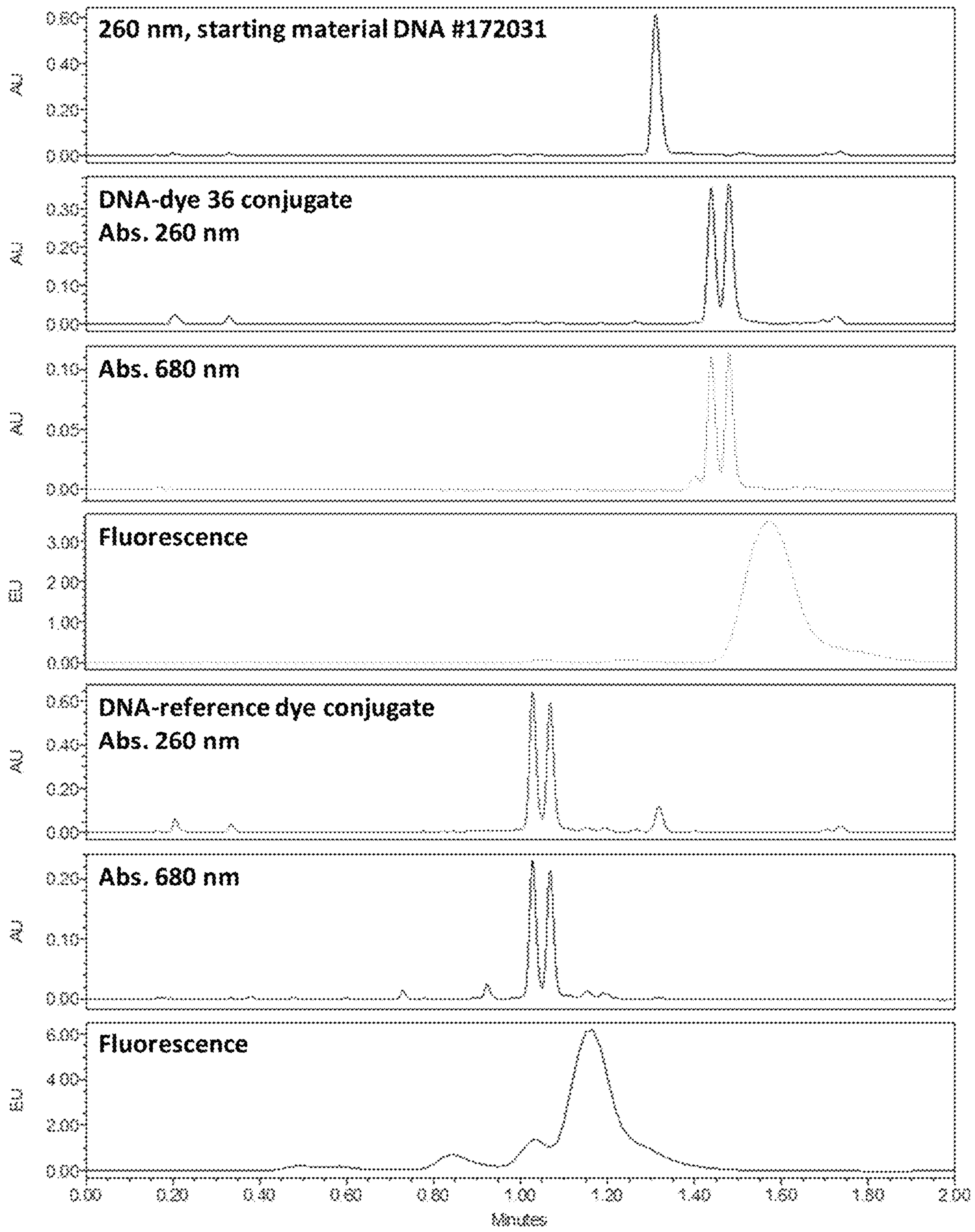
FIG. 2A: Shows UPLC chromatograms after labeling of DNA-probes with fluorescent dyes using strain-promoted azide-alkyne cycloaddition (click chemistry). The reaction between the DBCO and azide moieties generates triazole regioisomers that separate as double peaks in the chromatograms.
Figure 2B:
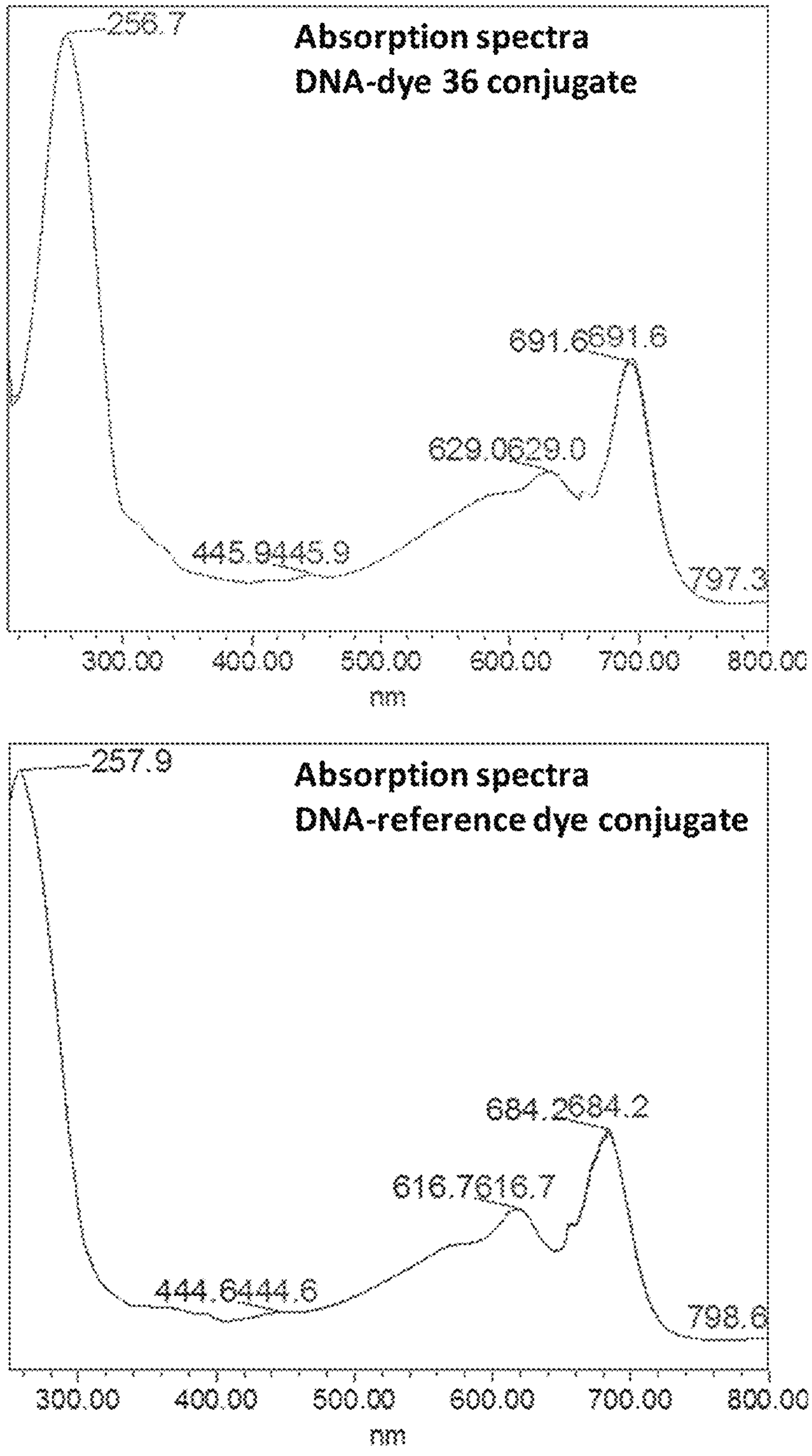
FIG. 2B: Shows the absorption spectra of DNA-dye conjugates, which were extracted from UPLC chromatogram peaks shown in FIG. 2A.

Dye labeled DNA probes were prepared by strain-promoted azide-alkyne cycloaddition between DNA-bound DBCO and azide-modified dye. Accordingly, a 30mer DNA probe containing a 3'-$C_3$ extension blocker, internal BHQ-2, and 5'-DBCO dT modification was prepared by solid-phase DNA synthesis and purified with standard methods. The DNA (1.0 eq., 100 μM, 50 mM TEAA) and the dye azide #36 (1.1 eq., 100 μM, 50 mM TEAA) were mixed and kept in a shaker for 2 h at RT. A DNA conjugate with a commercially available reference dye (azide-modified) was prepared in the same manner. Any dye excess was completely removed by ethanol precipitation using common procedures. UPLC analysis showed quantitative labeling of the DNA (FIGS. 2A and 2B).

Example 10: PCR Amplification Using Dye Labeled DNA Probes

Figure 3:
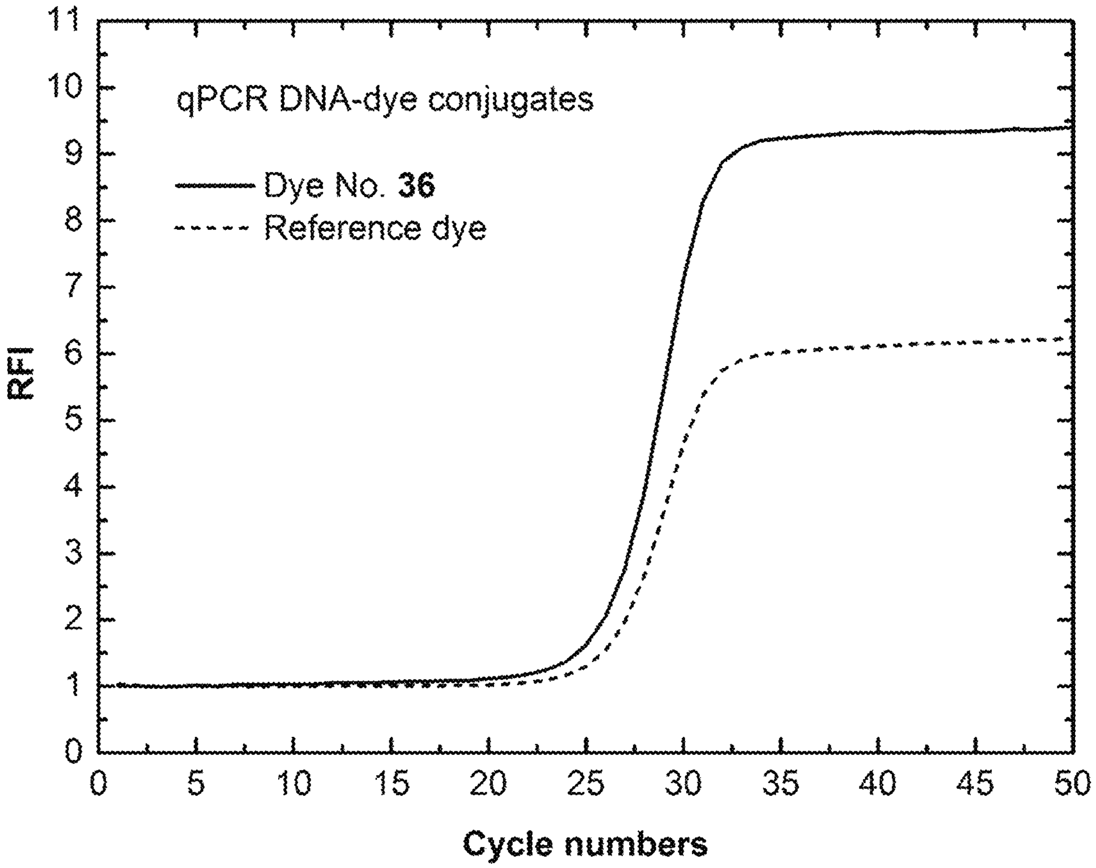
FIG. 3: Shows the growth curves for qPCR amplification using DNA probes that were labeled with dye No. 36 in comparison to a commercially available reference dye. The raw fluorescence signal was divided by total gain (RFI). Result: Dye No. 36 is compatible with qPCR and shows improved quenching by BHQ-2 compared to a commercially available dye in qPCR assays.

All qPCR components were prepared with nuclease-free $H_2O$. Reaction mixtures with a total volume of 50 μL were prepared by combining three components termed master mixture (20 μL), buffer mixture (20 μL), and dNTP mixture (10 μL). The master mixture contained tricine buffer (pH 8.2), manganese acetate, potassium acetate, glycerol, DMSO, detergent, target DNA (5000 copies/reaction), polymerase aptamer, labeled DNA probe, forward and reverse primer DNA, and polymerase enzyme. The dNTP mixture contained dATP, dCTP, dGTP (2.0 mM each), and dUTP (4.0 mM). Each qPCR was prepared as triplicate in the wells of a 96-well plate. The plate was sealed and subjected to amplification cycles with a LightCycler© 480 System (Fritz Hoffmann-La Roche, Basel, Switzerland). The growth curves were analyzed from fluorescence data collected in the Cy5.5 channel and are shown in FIG. 3.

Example 11: Immunohistochemical Tissue Staining

Figure 4:
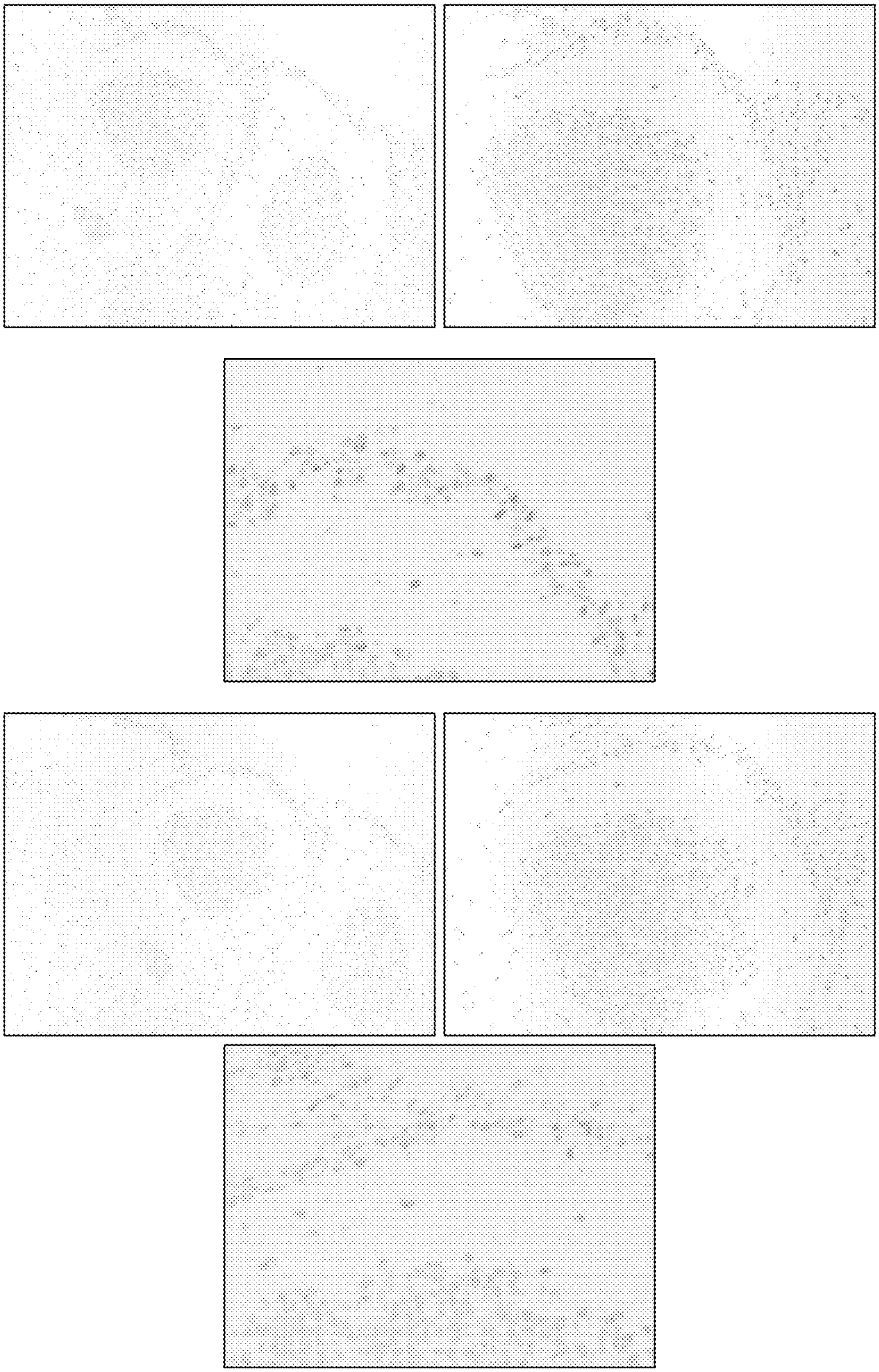
FIG. 4: Shows light microscopy images of immunohistochemically stained tonsil tissue sections at 10×, 20×, and 40× magnification (left to right). The sections of formalin fixed, paraffin embedded tissue were treated with CONFIRM™ anti-Ki-67 (30-9) Rabbit Monoclonal Primary Antibody (IgG), which is an abundant biomarker on tonsil tissue and directed against C-terminal portion of the Ki-67 antigen. Ki-67 is a nuclear protein expressed in proliferating cells. Staining for Ki-67 can be used to aid in assessing the proliferative activity of normal and neoplastic tissue. The dye azides No. 36 (top row) and reference dye CF680R (bottom row) were used for staining at 200 μM concentration. Result: The correct cellular structures were stained with no obvious background, demonstrating the compatibility of dye No. 36 with immunohistochemical tissue staining.

The dye azides No. 36 and CF680R were used for staining tonsil tissue sections. Sections of formalin fixed, paraffin embedded tissue were treated with CONFIRM™ anti-Ki-67 (30-9) Rabbit Monoclonal Primary Antibody (Ventana Medical Systems, Inc., Tucson, Az, U.S.A.) and labeled with the respective dye azides at 200 μM concentration. Light microscopy images at 10×, 20×, and 40× magnification are shown in FIG. 4.

The invention claimed is:

1. A fluorescent dye of Formula A or B

Formula A

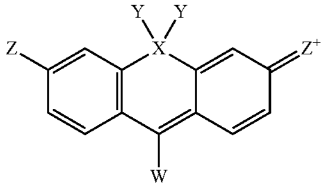

-continued

Formula B

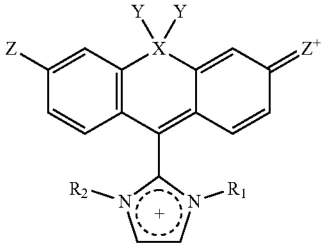

wherein:
X=Si, Ge, or C;
Y=Me, Et, iPr, or Ph;
Z=any one of:

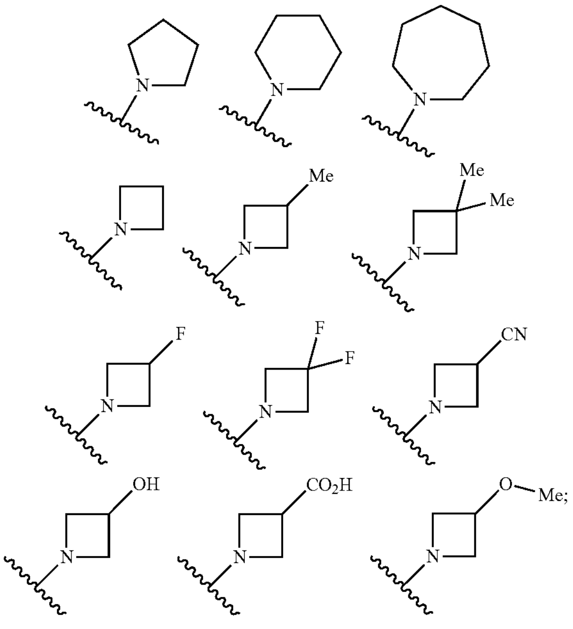

W=any one of:

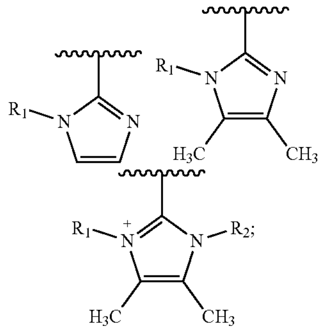

$R_1$ and $R_2$ are any combination of:

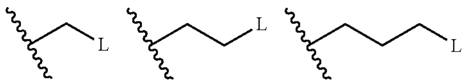

-continued
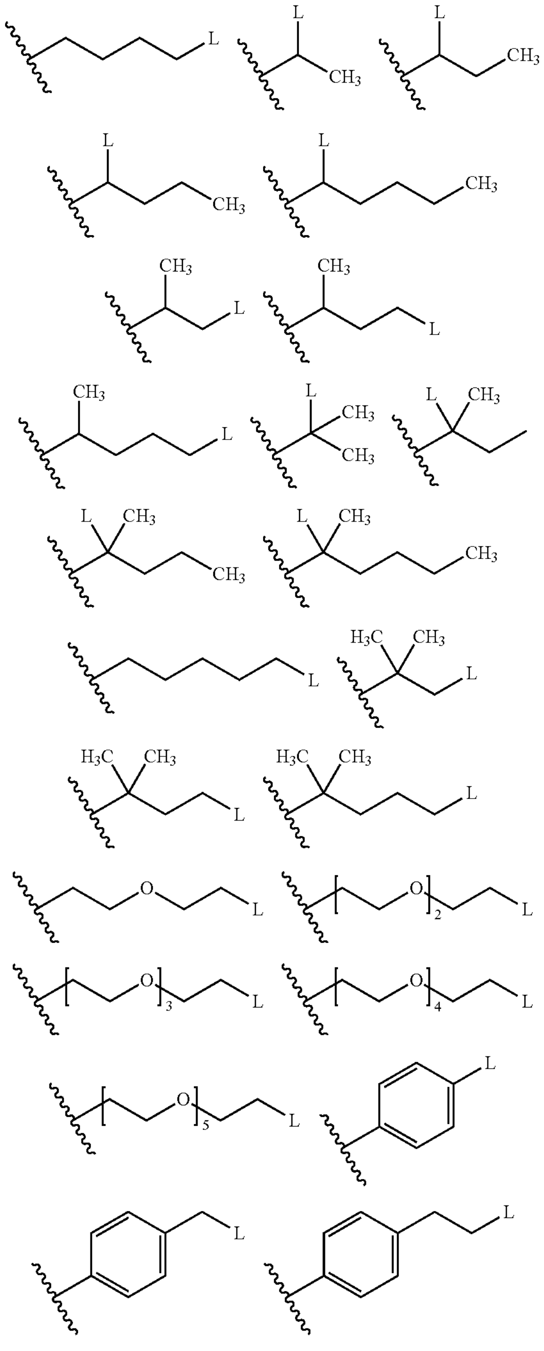
and L=H, $SO_3H$, $CONH_2$, $CO_2H$, $N_3$, or a moiety subject to click chemistry functionality selected from the group consisting of an alkyne and an azide.
2. The fluorescent dye of claim 1, wherein Z=any one of:
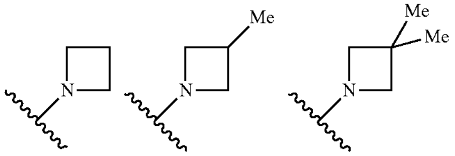
-continued
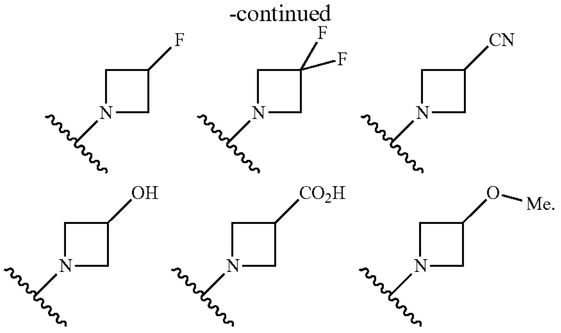
3. The fluorescent dye of claim 2, wherein Z=
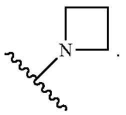
4. The fluorescent dye of claim 1, wherein the dye is selected from the group consisting of
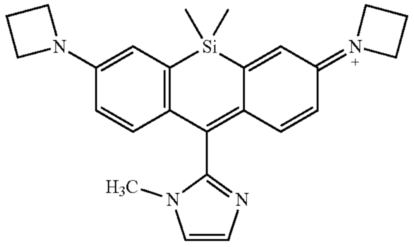
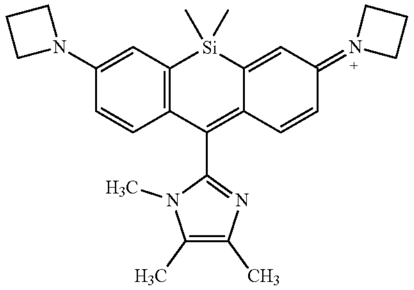
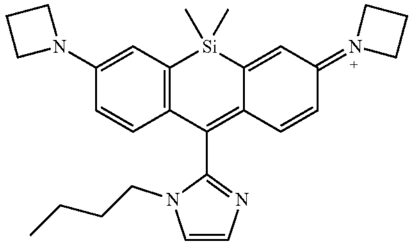
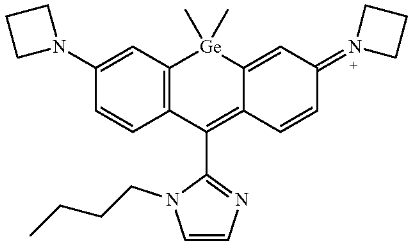

-continued

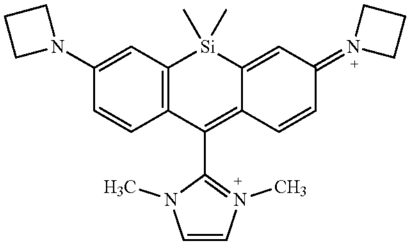

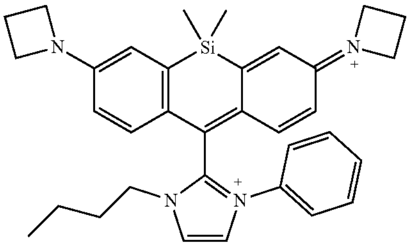

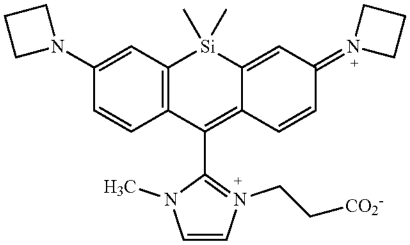

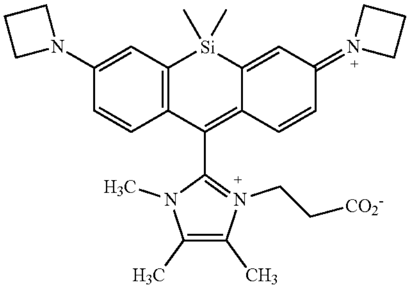

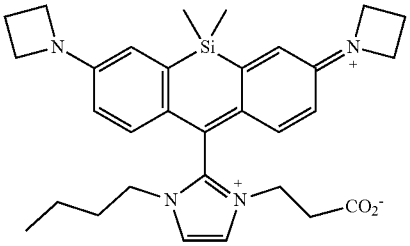

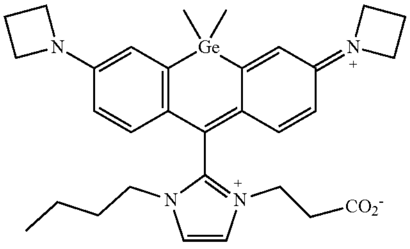

-continued

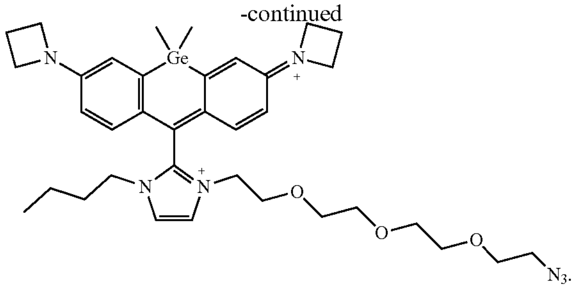

5. A method for preparing the fluorescent dyes of claim 1, the method comprising the steps of:

a) performing a double halogen-metal exchange of a dihalogenide to the corresponding dilithium compound with an organolithium reagent;

b) reacting the dilithium compound with an alkylester to form a hydroxyl-intermediate;

c) adding a Brønsted acid to the hydroxyl-intermediate for performing an aromatization by elimination of water to form an imidazole; and d) quarternization of the imidazole to imidazolium.

6. The method of claim 5, wherein quarternization is performed by nucleophilic substitution with an alkylhalogenide, alkyltosylate, alkyltriflate, or alkylmesylate.

7. The method of claim 5, wherein quarternization is performed with a cyclic lactone in the presence of a Lewis acid.

8. The method of claim 5, wherein quarternization is performed with in situ generated aryne from a 2-(trimethylsilyl) phenyl trifluoromethanesulfonate reagent and a fluoride donor.

9. A method of detecting the presence of one or more target nucleic acids in a sample in a polymerase chain reaction (PCR) assay by contacting said sample with an oligonucleotide probe labeled with at least one fluorescent dye of claim 1; and measuring a fluorescent signal generated from the labeled oligonucleotide whereby the detection of the fluorescent signal indicates the presence of the one or more target nucleic acids in the sample.

10. The method of claim 9, wherein the PCR assay is a multiplex PCR assay.

11. The method of claim 9, wherein measuring the fluorescent signal takes place at a temperature at or above 65° C.

12. A method of detecting the presence of one or more target proteins in a tissue sample in an immunohistochemical assay by contacting said tissue sample with a binding entity labeled with at least one fluorescent dye of claim 1 that directly or indirectly interacts with said target proteins; and visualizing a fluorescent signal generated in the tissue sample whereby the detection of the fluorescent signal indicates the presence of the one or more target protein in the tissue sample.

13. The method of claim 12, wherein the binding entity is a primary antibody that binds to the one or more target proteins or a secondary antibody that binds to the primary antibody.

* * * * *